(12) United States Patent
Flynn et al.

(10) Patent No.: US 9,012,635 B2
(45) Date of Patent: Apr. 21, 2015

(54) PYRIDONE AMIDES AND ANALOGS EXHIBITING ANTI-CANCER AND ANTI-PROLIFERATIVE ACTIVITIES

(71) Applicant: Deciphera Pharmaceuticals, LLC, Lawrence, KS (US)

(72) Inventors: Daniel L. Flynn, Lawrence, KS (US); Michael D. Kaufman, Lawrence, KS (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 0 days.

(21) Appl. No.: 14/214,127

(22) Filed: Mar. 14, 2014

(65) Prior Publication Data

US 2014/0343103 A1 Nov. 20, 2014

Related U.S. Application Data

(60) Provisional application No. 61/791,794, filed on Mar. 15, 2013.

(51) Int. Cl.
| | |
|---|---|
| *C07D 319/02* | (2006.01) |
| *C07D 401/00* | (2006.01) |
| *C07D 401/14* | (2006.01) |
| *A61K 31/505* | (2006.01) |
| *C07D 239/02* | (2006.01) |

(52) U.S. Cl.
CPC ............ *C07D 401/14* (2013.01); *A61K 31/505* (2013.01); *C07D 401/00* (2013.01); *C07D 239/02* (2013.01)

(58) Field of Classification Search
CPC ... C07D 401/14; C07D 239/02; C07D 401/00
USPC ........................................... 544/319; 546/256
See application file for complete search history.

(56) References Cited

U.S. PATENT DOCUMENTS

| | | | |
|---|---|---|---|
| 8,569,319 B2 * | 10/2013 | Flynn et al. .................. 514/269 |
| 2010/0120806 A1 | 5/2010 | Flynn et al. | |
| 2012/0172382 A1 | 7/2012 | Flynn et al. | |

OTHER PUBLICATIONS

International Search Report from corresponding International Application No. PCT/US2014/29638, dated Aug. 7, 2014.

* cited by examiner

*Primary Examiner* — Nizal Chandrakumar
(74) *Attorney, Agent, or Firm* — Cooley LLP

(57) ABSTRACT

Compounds useful in the treatment of mammalian cancers and especially human cancers according to Formula I are disclosed.

Formula I

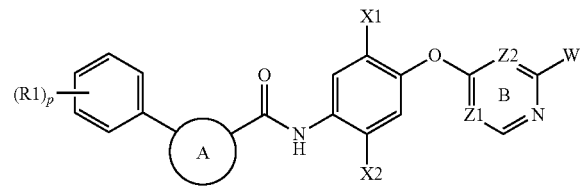

Pharmaceutical compositions and methods of treatment employing the compounds disclosed herein are also disclosed.

34 Claims, No Drawings

SEQUENCE LISTING

<160> NUMBER OF SEQ ID NOS: 4

<210> SEQ ID NO 1
<211> LENGTH: 676
<212> TYPE: PRT
<213> ORGANISM: Artificial Sequence
<220> FEATURE:
<223> OTHER INFORMATION: c-KIT with N-terminal GST fusion

<400> SEQUENCE: 1

```
Leu Gly Tyr Trp Lys Ile Lys Gly Leu Val Gln Pro Thr Arg Leu Leu
1               5                   10                  15
Leu Glu Tyr Leu Glu Glu Lys Tyr Glu Glu His Leu Tyr Glu Arg Asp
                20                  25                  30
Glu Gly Asp Lys Trp Arg Asn Lys Lys Phe Glu Leu Gly Leu Glu Phe
            35                  40                  45
Pro Asn Leu Pro Tyr Tyr Ile Asp Gly Asp Val Lys Leu Thr Gln Ser
    50                  55                  60
Met Ala Ile Ile Arg Tyr Ile Ala Asp Lys His Asn Met Leu Gly Gly
65                  70                  75                  80
Cys Pro Lys Glu Arg Ala Glu Ile Ser Met Leu Glu Gly Ala Val Asp
                85                  90                  95
Ile Arg Tyr Gly Val Ser Arg Ile Ala Tyr Ser Lys Asp Phe Glu Thr
            100                 105                 110
Leu Lys Val Asp Phe Leu Ser Lys Leu Pro Glu Met Leu Lys Met Phe
        115                 120                 125
Glu Asp Arg Leu Cys His Lys Thr Tyr Leu Asn Gly Asp His Val Thr
    130                 135                 140
His Pro Asp Phe Met Leu Tyr Asp Ala Leu Asp Val Val Leu Tyr Met
145                 150                 155                 160
Asp Pro Met Cys Leu Asp Ala Phe Pro Lys Leu Val Cys Phe Lys Lys
                165                 170                 175
Arg Ile Glu Ala Ile Pro Gln Ile Asp Lys Tyr Leu Lys Ser Ser Lys
            180                 185                 190
Tyr Ile Trp Pro Leu Gln Gly Trp Gln Ala Thr Phe Gly Gly Gly Asp
        195                 200                 205
His Pro Pro Lys Ser Asp Leu Val Pro Arg His Asn Gln Thr Ser Leu
    210                 215                 220
Tyr Lys Lys Ala Gly Ser Ala Ala Val Leu Glu Glu Asn Leu Tyr
225                 230                 235                 240
Phe Gln Gly Thr Tyr Lys Tyr Leu Gln Lys Pro Met Tyr Glu Val Gln
                245                 250                 255
Trp Lys Val Val Glu Glu Ile Asn Gly Asn Asn Tyr Val Tyr Ile Asp
            260                 265                 270
Pro Thr Gln Leu Pro Tyr Asp His Lys Trp Glu Phe Pro Arg Asn Arg
        275                 280                 285
Leu Ser Phe Gly Lys Thr Leu Gly Ala Gly Ala Phe Gly Lys Val Val
    290                 295                 300
Glu Ala Thr Ala Tyr Gly Leu Ile Lys Ser Asp Ala Ala Met Thr Val
305                 310                 315                 320
Ala Val Lys Met Leu Lys Pro Ser Ala His Leu Thr Glu Arg Glu Ala
                325                 330                 335
Leu Met Ser Glu Leu Lys Val Leu Ser Tyr Leu Gly Asn His Met Asn
            340                 345                 350
Ile Val Asn Leu Leu Gly Ala Cys Thr Ile Gly Gly Pro Thr Leu Val
```

```
                355                 360                 365
Ile Thr Glu Tyr Cys Cys Tyr Gly Asp Leu Leu Asn Phe Leu Arg Arg
370                 375                 380

Lys Arg Asp Ser Phe Ile Cys Ser Lys Gln Glu Asp His Ala Glu Ala
385                 390                 395                 400

Ala Leu Tyr Lys Asn Leu Leu His Ser Lys Glu Ser Ser Cys Ser Asp
                405                 410                 415

Ser Thr Asn Glu Tyr Met Asp Met Lys Pro Gly Val Ser Tyr Val Val
            420                 425                 430

Pro Thr Lys Ala Asp Lys Arg Ser Val Arg Ile Gly Ser Tyr Ile
        435                 440                 445

Glu Arg Asp Val Thr Pro Ala Ile Met Glu Asp Glu Leu Ala Leu
    450                 455                 460

Asp Leu Glu Asp Leu Leu Ser Phe Ser Tyr Gln Val Ala Lys Gly Met
465                 470                 475                 480

Ala Phe Leu Ala Ser Lys Asn Cys Ile His Arg Asp Leu Ala Ala Arg
                485                 490                 495

Asn Ile Leu Leu Thr His Gly Arg Ile Thr Lys Ile Cys Asp Phe Gly
            500                 505                 510

Leu Ala Arg Asp Ile Lys Asn Asp Ser Asn Tyr Val Lys Gly Asn
        515                 520                 525

Ala Arg Leu Pro Val Lys Trp Met Ala Pro Glu Ser Ile Phe Asn Cys
    530                 535                 540

Val Tyr Thr Phe Glu Ser Asp Val Trp Ser Tyr Gly Ile Phe Leu Trp
545                 550                 555                 560

Glu Leu Phe Ser Leu Gly Ser Ser Pro Tyr Pro Gly Met Pro Val Asp
                565                 570                 575

Ser Lys Phe Tyr Lys Met Ile Lys Glu Gly Phe Arg Met Leu Ser Pro
            580                 585                 590

Glu His Ala Pro Ala Glu Met Tyr Asp Ile Met Lys Thr Cys Trp Asp
        595                 600                 605

Ala Asp Pro Leu Lys Arg Pro Thr Phe Lys Gln Ile Val Gln Leu Ile
    610                 615                 620

Glu Lys Gln Ile Ser Glu Ser Thr Asn His Ile Tyr Ser Asn Leu Ala
625                 630                 635                 640

Asn Cys Ser Pro Asn Arg Gln Lys Pro Val Val Asp His Ser Val Arg
                645                 650                 655

Ile Asn Ser Val Gly Ser Thr Ala Ser Ser Ser Gln Pro Leu Leu Val
            660                 665                 670

His Asp Val
675

<210> SEQ ID NO 2
<211> LENGTH: 474
<212> TYPE: PRT
<213> ORGANISM: Homo sapiens

<400> SEQUENCE: 2

Met Ser Tyr Tyr His His His His His His Asp Tyr Asp Ile Pro Thr
1               5                   10                  15

Thr Glu Asn Leu Tyr Phe Gln Gly Ala Met Leu Val Pro Arg Gly Ser
            20                  25                  30

Pro Trp Ile Pro Phe Thr Met Lys Lys Arg Lys Gln Ile Lys Asp Leu
        35                  40                  45
```

```
Gly Ser Glu Leu Val Arg Tyr Asp Ala Arg Val His Thr Pro His Leu
 50                  55                  60
Asp Arg Leu Val Ser Ala Arg Ser Val Ser Pro Thr Thr Glu Met Val
 65                  70                  75                  80
Ser Asn Glu Ser Val Asp Tyr Arg Ala Thr Phe Pro Glu Asp Gln Phe
                 85                  90                  95
Pro Asn Ser Ser Gln Asn Gly Ser Cys Arg Gln Val Gln Tyr Pro Leu
                100                 105                 110
Thr Asp Met Ser Pro Ile Leu Thr Ser Gly Asp Ser Asp Ile Ser Ser
            115                 120                 125
Pro Leu Leu Gln Asn Thr Val His Ile Asp Leu Ser Ala Leu Asn Pro
130                 135                 140
Glu Leu Val Gln Ala Val Gln His Val Val Ile Gly Pro Ser Ser Leu
145                 150                 155                 160
Ile Val His Phe Asn Glu Val Ile Gly Arg Gly His Phe Gly Cys Val
                165                 170                 175
Tyr His Gly Thr Leu Leu Asp Asn Asp Gly Lys Lys Ile His Cys Ala
            180                 185                 190
Val Lys Ser Leu Asn Arg Ile Thr Asp Ile Gly Glu Val Ser Gln Phe
            195                 200                 205
Leu Thr Glu Gly Ile Ile Met Lys Asp Phe Ser His Pro Asn Val Leu
210                 215                 220
Ser Leu Leu Gly Ile Cys Leu Arg Ser Glu Gly Ser Pro Leu Val Val
225                 230                 235                 240
Leu Pro Tyr Met Lys His Gly Asp Leu Arg Asn Phe Ile Arg Asn Glu
                245                 250                 255
Thr His Asn Pro Thr Val Lys Asp Leu Ile Gly Phe Gly Leu Gln Val
            260                 265                 270
Ala Lys Gly Met Lys Tyr Leu Ala Ser Lys Lys Phe Val His Arg Asp
            275                 280                 285
Leu Ala Ala Arg Asn Cys Met Leu Asp Glu Lys Phe Thr Val Lys Val
290                 295                 300
Ala Asp Phe Gly Leu Ala Arg Asp Met Tyr Asp Lys Glu Tyr Tyr Ser
305                 310                 315                 320
Val His Asn Lys Thr Gly Ala Lys Leu Pro Val Lys Trp Met Ala Leu
                325                 330                 335
Glu Ser Leu Gln Thr Gln Lys Phe Thr Thr Lys Ser Asp Val Trp Ser
            340                 345                 350
Phe Gly Val Leu Leu Trp Glu Leu Met Thr Arg Gly Ala Pro Pro Tyr
            355                 360                 365
Pro Asp Val Asn Thr Phe Asp Ile Thr Val Tyr Leu Leu Gln Gly Arg
370                 375                 380
Arg Leu Leu Gln Pro Glu Tyr Cys Pro Asp Pro Leu Tyr Glu Val Met
385                 390                 395                 400
Leu Lys Cys Trp His Pro Lys Ala Glu Met Arg Pro Ser Phe Ser Glu
                405                 410                 415
Leu Val Ser Arg Ile Ser Ala Ile Phe Ser Thr Phe Ile Gly Glu His
            420                 425                 430
Tyr Val His Val Asn Ala Thr Tyr Val Asn Val Lys Cys Val Ala Pro
            435                 440                 445
Tyr Pro Ser Leu Leu Ser Ser Glu Asp Asn Ala Asp Asp Glu Val Asp
450                 455                 460
Thr Arg Pro Ala Ser Phe Trp Glu Thr Ser
```

```
465                 470

<210> SEQ ID NO 3
<211> LENGTH: 315
<212> TYPE: PRT
<213> ORGANISM: Homo sapiens

<400> SEQUENCE: 3

Asp Pro Asp Glu Leu Pro Leu Asp Glu His Cys Glu Arg Leu Pro Tyr
 1               5                  10                  15

Asp Ala Ser Lys Trp Glu Phe Pro Arg Asp Arg Leu Lys Leu Gly Lys
             20                  25                  30

Pro Leu Gly Arg Gly Ala Phe Gly Gln Val Ile Glu Ala Asp Ala Phe
         35                  40                  45

Gly Ile Asp Lys Thr Ala Thr Cys Arg Thr Val Ala Val Lys Met Leu
 50                  55                  60

Lys Glu Gly Ala Thr His Ser Glu His Arg Ala Leu Met Ser Glu Leu
 65                  70                  75                  80

Lys Ile Leu Ile His Ile Gly His His Leu Asn Val Val Asn Leu Leu
                 85                  90                  95

Gly Ala Cys Thr Lys Pro Gly Gly Pro Leu Met Val Ile Val Glu Phe
            100                 105                 110

Cys Lys Phe Gly Asn Leu Ser Thr Tyr Leu Arg Ser Lys Arg Asn Glu
        115                 120                 125

Phe Val Pro Tyr Lys Val Ala Pro Glu Asp Leu Tyr Lys Asp Phe Leu
    130                 135                 140

Thr Leu Glu His Leu Ile Cys Tyr Ser Phe Gln Val Ala Lys Gly Met
145                 150                 155                 160

Glu Phe Leu Ala Ser Arg Lys Cys Ile His Arg Asp Leu Ala Ala Arg
                165                 170                 175

Asn Ile Leu Leu Ser Glu Lys Asn Val Val Lys Ile Cys Asp Phe Gly
            180                 185                 190

Leu Ala Arg Asp Ile Tyr Lys Asp Pro Asp Tyr Val Arg Lys Gly Asp
        195                 200                 205

Ala Arg Leu Pro Leu Lys Trp Met Ala Pro Glu Thr Ile Phe Asp Arg
    210                 215                 220

Val Tyr Thr Ile Gln Ser Asp Val Trp Ser Phe Gly Val Leu Leu Trp
225                 230                 235                 240

Glu Ile Phe Ser Leu Gly Ala Ser Pro Tyr Pro Gly Val Lys Ile Asp
                245                 250                 255

Glu Glu Phe Cys Arg Arg Leu Lys Glu Gly Thr Arg Met Arg Ala Pro
            260                 265                 270

Asp Tyr Thr Thr Pro Glu Met Tyr Gln Thr Met Leu Asp Cys Trp His
        275                 280                 285

Gly Glu Pro Ser Gln Arg Pro Thr Phe Ser Glu Leu Val Glu His Leu
    290                 295                 300

Gly Asn Leu Leu Gln Ala Asn Ala Gln Gln Asp
305                 310                 315

<210> SEQ ID NO 4
<211> LENGTH: 435
<212> TYPE: PRT
<213> ORGANISM: Homo sapiens

<400> SEQUENCE: 4

Tyr Lys Tyr Lys Gln Lys Pro Lys Tyr Gln Val Arg Trp Lys Ile Ile
```

```
1               5                   10                  15
Glu Ser Tyr Glu Gly Asn Ser Tyr Thr Phe Ile Asp Pro Thr Gln Leu
            20                  25                  30

Pro Tyr Asn Glu Lys Trp Glu Phe Pro Arg Asn Asn Leu Gln Phe Gly
            35                  40                  45

Lys Thr Leu Gly Ala Gly Ala Phe Gly Lys Val Val Glu Ala Thr Ala
            50                  55                  60

Phe Gly Leu Gly Lys Glu Asp Ala Val Leu Lys Val Ala Val Lys Met
65                  70                  75                  80

Leu Lys Ser Thr Ala His Ala Asp Glu Lys Glu Ala Leu Met Ser Glu
            85                  90                  95

Leu Lys Ile Met Ser His Leu Gly Gln His Glu Asn Ile Val Asn Leu
            100                 105                 110

Leu Gly Ala Cys Thr His Gly Gly Pro Val Leu Val Ile Thr Glu Tyr
            115                 120                 125

Cys Cys Tyr Gly Asp Leu Leu Asn Phe Leu Arg Arg Lys Ala Glu Ala
            130                 135                 140

Met Leu Gly Pro Ser Leu Ser Pro Gly Gln Asp Pro Glu Gly Gly Val
145                 150                 155                 160

Asp Tyr Lys Asn Ile His Leu Glu Lys Lys Tyr Val Arg Arg Asp Ser
            165                 170                 175

Gly Phe Ser Ser Gln Gly Val Asp Thr Tyr Val Glu Met Arg Pro Val
            180                 185                 190

Ser Thr Ser Ser Asn Asp Ser Phe Ser Glu Gln Asp Leu Asp Lys Glu
            195                 200                 205

Asp Gly Arg Pro Leu Glu Leu Arg Asp Leu Leu His Phe Ser Ser Gln
            210                 215                 220

Val Ala Gln Gly Met Ala Phe Leu Ala Ser Lys Asn Cys Ile His Arg
225                 230                 235                 240

Asp Val Ala Ala Arg Asn Val Leu Leu Thr Asn Gly His Val Ala Lys
            245                 250                 255

Ile Gly Asp Phe Gly Leu Ala Arg Asp Ile Met Asn Asp Ser Asn Tyr
            260                 265                 270

Ile Val Lys Gly Asn Ala Arg Leu Pro Val Lys Trp Met Ala Pro Glu
            275                 280                 285

Ser Ile Phe Asp Cys Val Tyr Thr Val Gln Ser Asp Val Trp Ser Tyr
            290                 295                 300

Gly Ile Leu Leu Trp Glu Ile Phe Ser Leu Gly Leu Asn Pro Tyr Pro
305                 310                 315                 320

Gly Ile Leu Val Asn Ser Lys Phe Tyr Lys Leu Val Lys Asp Gly Tyr
            325                 330                 335

Gln Met Ala Gln Pro Ala Phe Ala Pro Lys Asn Ile Tyr Ser Ile Met
            340                 345                 350

Gln Ala Cys Trp Ala Leu Glu Pro Thr His Arg Pro Thr Phe Gln Gln
            355                 360                 365

Ile Cys Ser Phe Leu Gln Glu Gln Ala Gln Glu Asp Arg Arg Glu Arg
            370                 375                 380
```

-continued

```
Asp Tyr Thr Asn Leu Pro Ser Ser Ser Arg Ser Gly Gly Ser Gly Ser
385                 390                 395                 400

Ser Ser Ser Glu Leu Glu Glu Glu Ser Ser Ser Glu His Leu Thr Cys
                405                 410                 415

Cys Glu Gln Gly Asp Ile Ala Gln Pro Leu Leu Gln Pro Asn Asn Tyr
                420                 425                 430

Gln Phe Cys
        435
```

PYRIDONE AMIDES AND ANALOGS EXHIBITING ANTI-CANCER AND ANTI-PROLIFERATIVE ACTIVITIES

PRIORITY

This application claims the benefit of U.S. Provisional Application No. 61/791,794, filed Mar. 15, 2013. The entire disclosure of this application is relied on and incorporated into this application by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: DECP_047_01US_SeqList_ST25.txt, date recorded: Mar. 15, 2014, file size 20 kilobytes).

FIELD OF THE INVENTION

The present invention relates to kinase inhibitors exhibiting properties useful for the treatment of various diseases including hyperproliferative diseases and cancer. More particularly, the invention is concerned with such compounds, methods of treating diseases, methods of synthesis of the compounds, and methods of manufacturing the compounds. Preferably, the compounds are useful for the modulation of activity of c-MET kinase, c-MET kinase polymorphs, c-MET kinase mutants, or c-MET kinase fusion proteins in the treatment of mammalian diseases, and in particular human cancers.

BACKGROUND OF THE INVENTION c-MET is a receptor tyrosine kinase (RTK) located on chromosome 7p and activated via its natural ligand hepatocyte growth factor. c-MET is found mutated in a variety of solid tumors (Ma, P. C. et al. *Cancer Metastasis* (2003) 22: 309). Mutations in the tyrosine kinase domain are associated with hereditary papillary renal cell carcinomas (Schmidt, L. et al. *Nat. Genet.* (1997) 16: 68; Schmidt, L. et al. *Oncogene* (1999) 18: 2343), whereas mutations in the sema and juxtamembrane domains are often found in small cell lung cancers (Ma, P. C. et al. *Cancer Res.* (2003) 63: 6272). Many activating mutations are also found in breast cancers (Nakopoulou, et al. *Histopath.* (2000) 36(4): 313). The panoply of tumor types for which c-MET mediated growth has been implicated suggests this is a target ideally suited for modulation by specific c-MET small molecule inhibitors.

The TPR-MET oncogene is a transforming variant of the c-MET RTK and was initially identified after treatment of a human osteogenic sarcoma cell line transformed by the chemical carcinogen N-methyl-N'-nitro-N-nitrosoguanidine (Park, M. et al. *Cell* (1986) 45: 895). The TPR-MET fusion oncoprotein is the result of a chromosomal translocation, placing the TPR3 locus on chromosome 1 upstream of a portion of the c-MET gene on chromosome 7 encoding only for the cytoplasmic region. Studies suggest that TPR-MET is detectable in experimental cancers (e.g., Yu, J. et al. *Cancer* (2000) 88: 1801). Dimerization of the $M_r$ 65,000 TPR-MET oncoprotein through a leucine zipper motif encoded by TPR leads to constitutive activation of the c-MET kinase (Zhen, Z. et al. *Oncogene* (1994) 9: 1691). TPR-MET activates wild-type c-MET RTK and can activate crucial cellular growth pathways, including the Ras pathway (Aklilu, F. et al. *Am. J. Physiol.* (1996) 271: E277) and the phosphatidylinositol 3-kinase (PI3K)/AKT pathway (Ponzetto, C. et al. *Mol. Cell. Biol.* (1993) 13: 4600). Conversely, in contrast to c-MET RTK, TPR-MET is ligand independent, lacks the CBL-like SH2 domain binding site in the juxtamembrane region in c-MET, and is mainly cytoplasmic. c-MET immunohistochemical expression seems to be associated with abnormal β-catenin expression, a hallmark feature of epithelial to mesenchymal transition (EMT) and provides good prognostic and predictive factors in breast cancer patients.

In human therapeutics, it is desirable to provide small molecule inhibitors of a protein target within a protein family which do not cross-inhibit closely related protein family members. These closely related protein family members are often referred to as 'off-targets', to distinguish them from the essential target of interest referred to as the 'on target' of the inhibitor. A small molecule which inhibits multiple protein family members, while being potent against the target of interest, can be limited in its utility as a human therapeutic due to unintended side effects and toxicities introduced due to the consequences of inhibition of these 'off targets.'

Protein kinases constitute an important therapeutic protein family. There are approximately 518 human protein kinases. While inhibition of a desired kinase 'on target' is desirable for a human therapeutic, it is also desirable in many cases to provide a selective kinase inhibitor which does not substantially inhibit other kinase 'off targets' from within this protein family. Monoclonal antibodies are one approach to providing specific inhibitors to a specific kinase without inhibiting 'off targets.' Achieving this level of selectivity with small molecule inhibitors, however, is not as easily achievable nor as straightforward. Accordingly, there is a need for kinase inhibitors that are selective for a particular protein kinase. It is theorized that an unexpected increase in potency for c-MET kinase inhibition or an unexpected increase in selective c-MET inhibition relative to other kinases is observed for one or more of the embodiments disclosed herein.

SUMMARY OF THE INVENTION

Compounds described herein find utility in the treatment of mammalian cancers and especially human cancers including, but not limited to, solid tumors, gastric cancers, melanomas, glioblastomas, ovarian cancer, pancreatic cancer, prostate cancer, lung cancers, non small cell lung cancer, breast cancers, kidney cancers, cervical carcinomas, metastasis of primary tumor sites, colonic cancers, myeloproliferative diseases, diseases wherein the etiology or progression is dependent on c-MET kinase activity, or on the activity of oncogenic forms, aberrant fusion protein forms, and mutant forms of c-MET kinase.

Specifically, pyridone amide compounds of Formula I are disclosed which find utility in the treatment of diseases as described above.

Formula I

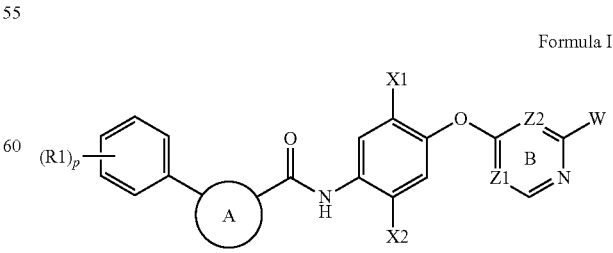

and pharmaceutically acceptable salts, enantiomers, stereoisomers or tautomers thereof wherein A is

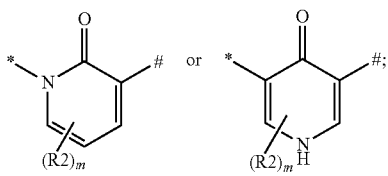

wherein the "*" is connected to the R1-substituted phenyl ring and the "#" is connected to the amide carbonyl; and R1, R2, m, p, X1, X2, W, Z1, and Z2 are as defined below for Formula I.

Accordingly, in one aspect, the present invention comprises a compound of Formula I, Formula I

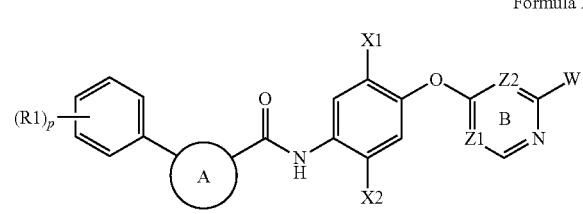

or a pharmaceutically acceptable salt, enantiomer, stereoisomer or tautomer thereof, wherein:

A is

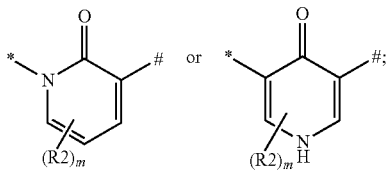

wherein the "*" is connected to the R1-substituted phenyl ring and the "#" is connected to the amide carbonyl;
W is —(CH$_2$)$_n$-pyrazole optionally substituted with —(R3)$_q$;
X1 is halogen or C1-C6 alkyl;
X2 is halogen or C1-C6 alkyl;
each R1 is individually and independently halogen, H, C1-C6 alkyl, C3-C8 branched alkyl, C3-C8 cycloalkyl, C1-C6 alkoxy, branched C3-C6 alkoxy, or cyano;
each R2 is individually and independently C1-C6 alkoxy, C1-C6 alkylamino, H, halogen, C1-C6 alkyl, C3-C8 branched alkyl, C3-C8 cycloalkyl, branched C3-C6 alkoxy, branched C3-C6 alkylamino, or cyano;
each R3 is individually and independently C1-C6 alkyl, branched C3-C8 alkyl, halogen, —(CH$_2$)$_r$—CN, —(CH$_2$)$_r$—OR6, —(CH$_2$)$_r$—NR6(R7), —(CH$_2$)$_r$—SO$_2$—C1-C6-alkyl, —(CH$_2$)$_r$—C(O)NR6(R7), —(CH$_2$)$_r$—C(O)—C4-C6-heterocyclyl, or —(CH$_2$)$_r$—C4-C6-heterocyclyl, wherein each alkyl or alkylene is optionally substituted with one or two C1-C6 alkyl;
Z1 is CR4 or N;
Z2 is CR5 or N;
with the proviso that only one of Z1 and Z2 are simultaneously N;
R4 and R5 are individually and independently H, halogen, C1-C6 alkyl, C3-C8 branched alkyl, C3-C8 cycloalkyl, C1-C6 alkoxy, branched C3-C6 alkoxy, or cyano;

each R6 and R7 is individually and independently H, C1-C6 alkyl, or branched C3-C8 alkyl;
m is 0, 1, or 2;
n is 0, 1, or 2;
p is 1, 2, or 3;
q is 0, 1, or 2; and
r is 0, 1, or 2.

In some embodiments, the compound of Formula I is a compound of Formula Ia,

Formula Ia

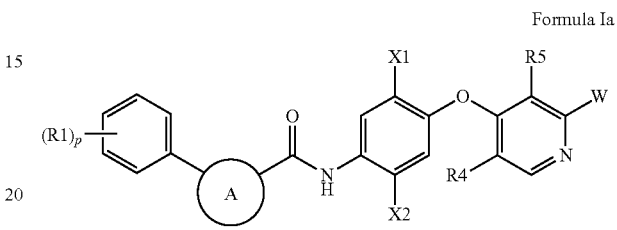

or a pharmaceutically acceptable salt, enantiomer, stereoisomer or tautomer thereof.

In some embodiments, the compound of Formula Ia is a compound of Formula Ib,

Formula Ib

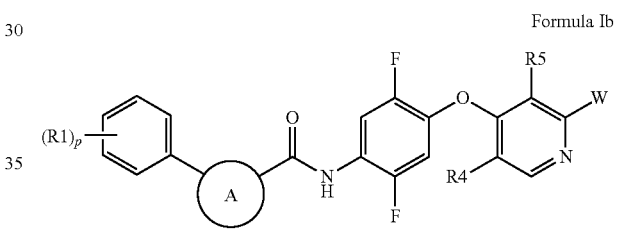

or a pharmaceutically acceptable salt, enantiomer, stereoisomer or tautomer thereof.

In some embodiments of the compound of Formula Ib, p is 1 and R1 is para-fluoro.

In some embodiments of the compound of Formula Ib, both R4 and R5 are H.

In some embodiments of the compound of Formula Ib, R4 is H and R5 is not H.

In some embodiments of the compound of Formula Ib, W is

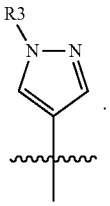

In some embodiments of the compound of Formula Ib, R3 is C1-C6 alkyl or branched C3-C8 alkyl.

In some embodiments of the compound of Formula Ib, R3 is C1-C6 alkyl.

In some embodiments of the compound of Formula Ib, R3 is methyl.

In some embodiments of the compound of Formula Ib, the A ring is

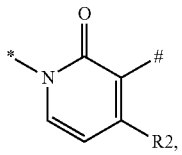

and R2 is C1-C6 alkoxy.

In some embodiments of the compound of Formula Ib, the A ring is

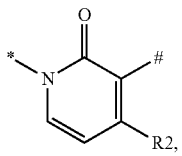

and R2 is ethoxy.

In some embodiments of the compound of Formula Ib, the compound has the Formula;

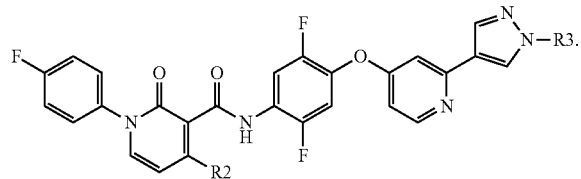

In some embodiments of the compound of Formula Ib, the compound is

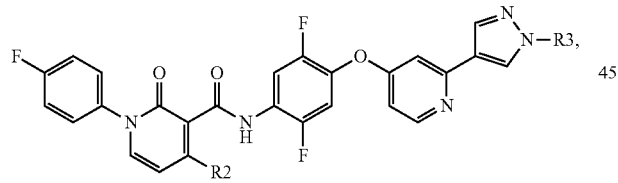

R2 is C1-C6 alkoxy, and R3 is C1-C6 alkyl or branched C3-C8 alkyl.

In one embodiment of the compound of Formula Ib, the compound is

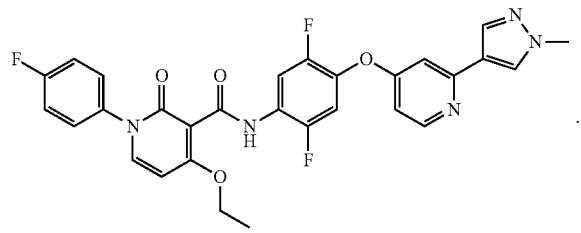 [SMILES: CCOc1ccn(-c2ccc(F)cc2)c(=O)c1C(=O)Nc1cc(F)c(Oc2ccnc(-c3cnn(C)c3)c2)cc1F]

In some embodiments of the compound of Formula I, the compound is a compound of Formula Ic,

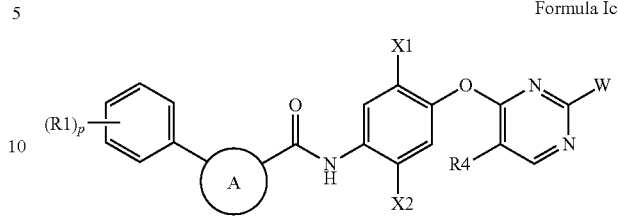

Formula Ic or a pharmaceutically acceptable salt, enantiomer, stereoisomer or tautomer thereof.

In some embodiments of the compound of Formula Ic, the compound is a compound of Formula Id,

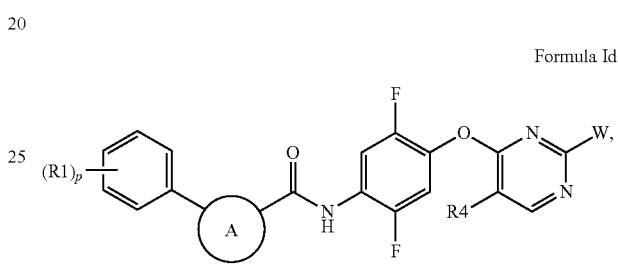

Formula Id or a pharmaceutically acceptable salt, enantiomer, stereoisomer or tautomer thereof.

In some embodiments of the compound of Formula Id, R4 is H.

In some embodiments of the compound of Formula Id, W is

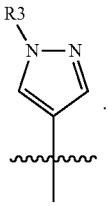

In some embodiments of the compound of Formula Id, R3 is C1-C6 alkyl or branched C3-C8 alkyl.

In some embodiments of the compound of Formula Id, R3 is C1-C6 alkyl.

In some embodiments of the compound of Formula Id, R3 is methyl.

In some embodiments of the compound of Formula Id, the A ring is

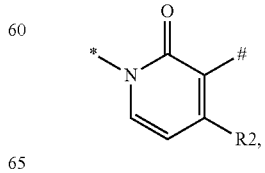

and R2 is C1-C6 alkoxy.

In some embodiments of the compound of Formula Id, the A ring is

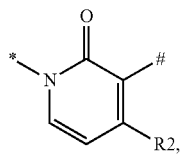

and R2 is ethoxy.

In some embodiments of the compound of Formula Id, the compound has the Formula

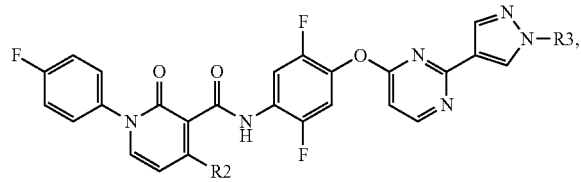

or a pharmaceutically acceptable salt, enantiomer, stereoisomer or tautomer thereof.

In some embodiments of the compound of Formula Id, the compound is

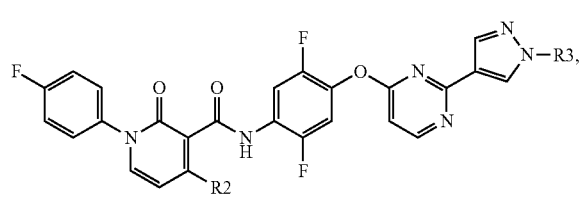

R2 is C1-C6 alkoxy and R3 is C1-C6 alkyl or branched C3-C8 alkyl, or a pharmaceutically acceptable salt, enantiomer, stereoisomer or tautomer thereof In one embodiment of the compound of Formula Id, the compound is

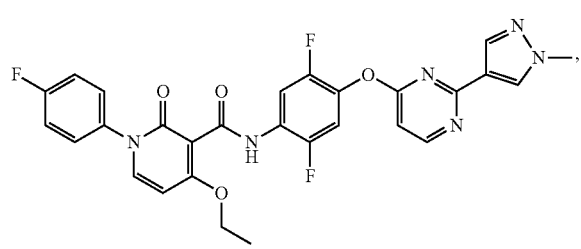 [SMILES: CCOc1ccn(-c2ccc(F)cc2)c(=O)c1C(=O)Nc1cc(F)c(Oc2ccnc(-c3cnn(C)c3)n2)cc1F]

or a pharmaceutically acceptable salt, enantiomer, stereoisomer or tautomer thereof.

In some embodiments of the compound of Formula I, the compound is a compound of Formula Ie, Formula Ie

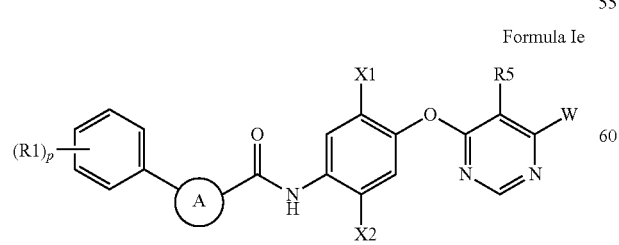

or a pharmaceutically acceptable salt, enantiomer, stereoisomer or tautomer thereof.

In some embodiments of the compound of Formula Ie, the compound is a compound of Formula If, Formula If

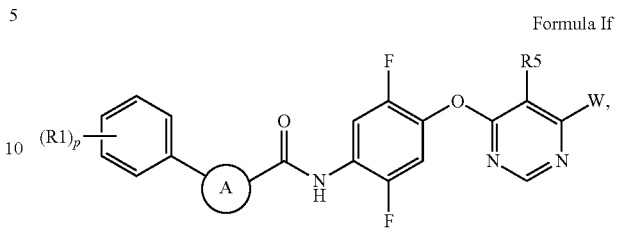

or a pharmaceutically acceptable salt, enantiomer, stereoisomer or tautomer thereof.

In some embodiments of the compound of Formula If, R5 is H.

In some embodiments of the compound of Formula If, W is

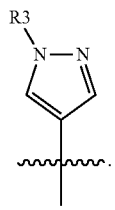

In some embodiments of the compound of Formula If, R3 is C1-C6 alkyl or branched C3-C8 alkyl.

In some embodiments of the compound of Formula If, R3 is C1-C6 alkyl.

In some embodiments of the compound of Formula If, R3 is methyl.

In some embodiments of the compound of Formula If, the A ring is

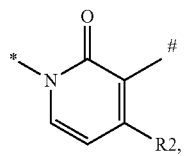

and R2 is C1-C6 alkoxy.

In some embodiments of the compound of Formula If, the A ring is

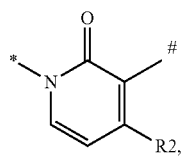

and R2 is ethoxy.

In some embodiments of the compound of Formula If, the compound has the Formula

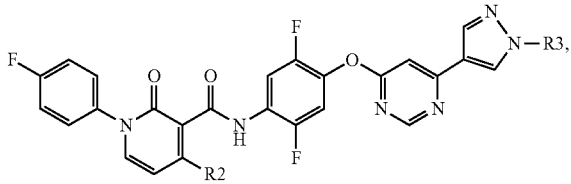

or a pharmaceutically acceptable salt, enantiomer, stereoisomer or tautomer thereof In some embodiments of the compound of Formula If, the compound is

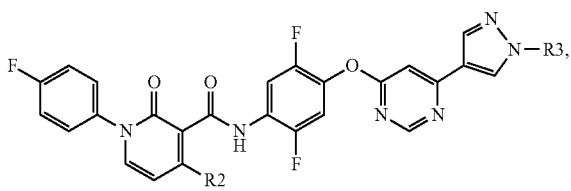

R2 is C1-C6 alkoxy, and R3 is C1-C6 alkyl or branched C3-C8 alkyl, or a pharmaceutically acceptable salt, enantiomer, stereoisomer or tautomer thereof In one embodiment of the compound of Formula If, the compound is

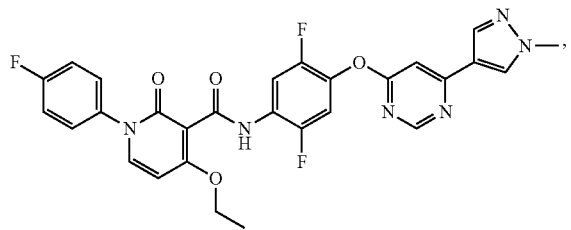 [SMILES: CCOc1ccn(-c2ccc(F)cc2)c(=O)c1C(=O)Nc1cc(F)c(Oc2cc(-c3cnn(C)c3)ncn2)cc1F]

or a pharmaceutically acceptable salt, enantiomer, stereoisomer or tautomer thereof.

In some embodiments, the invention comprises a compound selected from the group consisting of N-(2,5-difluoro-4-((2-(1-methyl-1H-pyrazol-4-yl)pyridin-4-yl)oxy)phenyl)-1-(4-fluorophenyl)-2-oxo-1,2-dihydropyridine-3-carboxamide, N-(2,5-difluoro-4-(2-(1-methyl-1H-pyrazol-4-yl)pyridin-4-yloxy)phenyl)-4-ethoxy-1-(4-fluorophenyl)-2-oxo-1,2-dihydropyridine-3-carboxamide, N-(2,5-difluoro-4-((2-(1-(2-hydroxyethyl)-1H-pyrazol-4-yl)pyridin-4-yl)oxy)phenyl)-1-(4-fluorophenyl)-2-oxo-1,2-dihydropyridine-3-carboxamide, N-(2,5-difluoro-4-((2-(1-methyl-1H-pyrazol-4-yl)pyridin-4-yl)oxy)phenyl)-1-(4-fluorophenyl)-4-(methylamino)-2-oxo-1,2-dihydropyridine-3-carboxamide, N-(2,5-difluoro-4-((2-(1-methyl-1H-pyrazol-4-yl)pyridin-4-yl)oxy)phenyl)-4-(ethylamino)-1-(4-fluorophenyl)-2-oxo-1,2-dihydropyridine-3-carboxamide, N-(2,5-difluoro-4-((2-(1-isopropyl-1H-pyrazol-4-yl)pyridin-4-yl)oxy)phenyl)-4-ethoxy-1-(4-fluorophenyl)-2-oxo-1,2-dihydropyridine-3-carboxamide, 4-ethoxy-N-(4-((2-(1-ethyl-1H-pyrazol-4-yl)pyridin-4-yl)oxy)-2,5-difluorophenyl)-1-(4-fluorophenyl)-2-oxo-1,2-dihydropyridine-3-carboxamide, N-(4-((2-(1H-pyrazol-4-yl)pyridin-4-yl)oxy)-2,5-difluorophenyl)-4-ethoxy-1-(4-fluorophenyl)-2-oxo-1,2-dihydropyridine-3-carboxamide, N-(2,5-difluoro-4-((2-(1-methyl-1H-pyrazol-4-yl)pyridin-4-yl)oxy)phenyl)-5-(4-fluorophenyl)-1-methyl-4-oxo-1,4-dihydropyridine-3-carboxamide, and N-(2,5-difluoro-4-((2-(1-methyl-1H-pyrazol-4-yl)pyridin-4-yl)oxy)phenyl)-5-(4-fluorophenyl)-4-oxo-1,4-dihydropyridine-3-carboxamide, or a pharmaceutically acceptable salt, enantiomer, stereoisomer or tautomer thereof.

In certain embodiments, the disease etiology or progression is at least partially mediated by the kinase activity of c-MET, mutant oncogenic forms, aberrant fusion proteins, or polymorphs thereof.

In other embodiments, the present invention comprises a pharmaceutical composition, comprising a compound of Formula I and a pharmaceutically acceptable carrier.

In certain embodiments, the composition comprises an additive selected from adjuvants, excipients, diluents, or stabilizers.

In some embodiments, the invention includes a method of treating cancer, gastrointestinal stromal tumors, hyperproliferative diseases, metabolic diseases, neurodegenerative diseases, or diseases characterized by angiogenesis, solid tumors, melanomas, gliomas, glioblastomas, ovarian cancer, pancreatic cancer, prostate cancer, lung cancers, breast cancers, renal cancers, hepatic cancers, cervical carcinomas, metastasis of primary tumor sites, myeloproliferative diseases, chronic myelogenous leukemia, leukemias, papillary thyroid carcinoma, non-small cell lung cancer, mesothelioma, hypereosinophilic syndrome, colonic cancers, ocular diseases characterized by hyperproliferation leading to blindness including retinopathies, diabetic retinopathy, age-related macular degeneration, hypereosinophilic syndrome, rheumatoid arthritis, asthma, chronic obstructive pulmonary, mastocytosis, or mast cell leukemia, the method comprising administering to a patient in need thereof an effective amount of a compound of Formula I.

In some embodiments, the invention includes a method of treating melanomas, gliomas, glioblastomas, ovarian cancer, pancreatic cancer, prostate cancer, lung cancers, breast cancers, renal cancers, hepatic cancers, cervical carcinomas, metastasis of primary tumor sites, non-small cell lung cancer, or colonic cancers, the method comprising administering to a patient in need thereof an effective amount of a compound of Formula I.

In certain embodiments of the present methods, the compound is administered orally, parenterally, by inhalation, or subcutaneously.

In some embodiments, the invention provides a compound of Formula I, or a pharmaceutically acceptable salt thereof, for use in therapy. In some embodiments, the invention provides the use of a compound of Formula I, or a pharmaceutically acceptable salt thereof, in therapy to treat cancer, gastrointestinal stromal tumors, hyperproliferative diseases, metabolic diseases, neurodegenerative diseases, or diseases characterized by angiogenesis, solid tumors, melanomas, gliomas, glioblastomas, ovarian cancer, pancreatic cancer, prostate cancer, lung cancers, breast cancers, renal cancers, hepatic cancers, cervical carcinomas, metastasis of primary tumor sites, myeloproliferative diseases, chronic myelogenous leukemia, leukemias, papillary thyroid carcinoma, non-small cell lung cancer, mesothelioma, hypereosinophilic syndrome, colonic cancers, ocular diseases characterized by hyperproliferation leading to blindness including retinopathies, diabetic retinopathy, age-related macular degeneration, hypereosinophilic syndrome, rheumatoid arthritis, asthma, chronic obstructive pulmonary, mastocytosis, or mast cell leukemia.

In some embodiments, the invention provides the use of a compound of Formula I, or a pharmaceutically acceptable salt thereof, in therapy to treat melanomas, gliomas, glioblastomas, ovarian cancer, pancreatic cancer, prostate cancer, lung cancers, breast cancers, renal cancers, hepatic cancers, cervical carcinomas, metastasis of primary tumor sites, non-small cell lung cancer, or colonic cancers.

In some embodiments, the invention provides for the use of a compound of Formula I, or a pharmaceutically acceptable salt thereof, for the manufacture of a medicament for the treatment of cancer, gastrointestinal stromal tumors, hyperproliferative diseases, metabolic diseases, neurodegenerative diseases, or diseases characterized by angiogenesis, such as solid tumors, melanomas, gliomas, glioblastomas, ovarian cancer, pancreatic cancer, prostate cancer, lung cancers, breast cancers, renal cancers, hepatic cancers, cervical carcinomas, metastasis of primary tumor sites, myeloproliferative diseases, chronic myelogenous leukemia, leukemias, papillary thyroid carcinoma, non-small cell lung cancer, mesothelioma, hypereosinophilic syndrome, colonic cancers, ocular diseases characterized by hyperproliferation leading to blindness including retinopathies, diabetic retinopathy, age-related macular degeneration, hypereosinophilic syndrome, rheumatoid arthritis, asthma, chronic obstructive pulmonary, mastocytosis, or mast cell leukemia. Yet in other embodiments, the invention provides for the use of a compound of Formula I, or a pharmaceutically acceptable salt thereof, for the manufacture of a medicament for the treatment of melanomas, gliomas, glioblastomas, ovarian cancer, pancreatic cancer, prostate cancer, lung cancers, breast cancers, renal cancers, hepatic cancers, cervical carcinomas, metastasis of primary tumor sites, non-small cell lung cancer, or colonic cancers.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

DETAILED DESCRIPTION OF THE INVENTION

Throughout this disclosure, various patents, patent applications, and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The compounds of this disclosure include any and all possible isomers, stereoisomers, enantiomers, diastereomers, tautomers, and pharmaceutically acceptable salts thereof. Thus, the terms "compound" and "compounds" as used in this disclosure refer to the compounds of this disclosure and any and all possible isomers, stereoisomers, enantiomers, diastereomers, tautomers, and pharmaceutically acceptable salts thereof.

DEFINITIONS

The term "alkyl" as used herein refers to a straight chain alkyl, wherein alkyl chain length is indicated by a range of numbers. In exemplary embodiments, "alkyl" refers to an alkyl chain as defined above containing 1, 2, 3, 4, 5, or 6 carbons (i.e., C1-C6 alkyl). Examples of an alkyl group include, but are not limited to, methyl, ethyl, propyl, butyl, pentyl, and hexyl.

The term "branched alkyl" as used herein refers to an alkyl chain wherein a branching point in the chain exists, and the total number of carbons in the chain is indicated by a range of numbers. In exemplary embodiments, "branched alkyl" refers to an alkyl chain as defined above containing from 3, 4, 5, 6, 7, or 8 carbons (i.e., branched C3-C8 alkyl). Examples of a branched alkyl group include, but are not limited to, iso-propyl, iso-butyl, secondary-butyl, and tertiary-butyl.

The term "alkoxy" as used herein refers to —O-(alkyl), wherein "alkyl" is as defined above.

The term "branched alkoxy" as used herein refers to —O-(branched alkyl), wherein "branched alkyl" is as defined above.

The term "alkylene" as used herein refers to an alkyl moiety interposed between two other atoms. In exemplary embodiments, "alkylene" refers to an alkyl moiety as defined above containing 1, 2, or 3 carbons. Examples of an alkylene group include, but are not limited to —CH$_2$—, —CH$_2$CH$_2$—, and —CH$_2$CH$_2$CH$_2$—. In exemplary embodiments, alkylene groups are branched.

The term "alkynyl" as used herein refers to a carbon chain containing one carbon-carbon triple bond. In exemplary embodiments, "alkynyl" refers to a carbon chain as described above containing 2 or 3 carbons (i.e., C2-C3 alkynyl). Examples of an alkynyl group include, but are not limited to, ethyne and propyne.

The term "aryl" as used herein refers to a cyclic hydrocarbon, where the ring is characterized by delocalized π electrons (aromaticity) shared among the ring members, and wherein the number of ring atoms is indicated by a range of numbers. In exemplary embodiments, "aryl" refers to a cyclic hydrocarbon as described above containing 6, 7, 8, 9, or 10 ring atoms (i.e., C6-C10 aryl). Examples of an aryl group include, but are not limited to, benzene, naphthalene, tetralin, indene, and indane.

The term "cycloalkyl" as used herein refers to a monocyclic saturated carbon ring, wherein the number of ring atoms is indicated by a range of numbers. In exemplary embodiments, "cycloalkyl" refers to a carbon ring as defined above containing 3, 4, 5, 6, 7, or 8 ring atoms (i.e., C3-C8 cycloalkyl). Examples of a cycloalkyl group include, but are not limited to, cyclopropyl, cyclobutyl, cyclopentyl, cyclohexyl, cycloheptyl, and cyclooctyl.

The term "halogen" as used herein refers to fluorine, chlorine, bromine, and iodine.

The term "heterocycle" or "heterocyclyl" as used herein refers to a cyclic hydrocarbon, wherein at least one of the ring atoms is an O, N, or S, wherein the number of ring atoms is indicated by a range of numbers. Heterocyclyl moieties as defined herein have C or N bonding hands. For example, in some embodiments, a ring N atom from the heterocyclyl is the bonding atom to —C(O) to form an amide, carbamate, or urea. In exemplary embodiments, "heterocyclyl" refers to a cyclic hydrocarbon as described above containing 4, 5, or 6 ring atoms (i.e., C4-C6 heterocyclyl). Examples of a heterocycle group include, but are not limited to, aziridine, oxirane, thiirane, azetidine, oxetane, thietane, pyrrolidine, tetrahydrofuran, pyran, thiopyran, thiomorpholine, thiomorpholine S-oxide, thiomorpholine S-dioxide, oxazoline, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to a cyclic hydrocarbon, where at least one of the ring atoms is an O, N, or S, the ring is characterized by delocalized π electrons (aromaticity) shared among the ring members, and wherein the number of ring atoms is indicated by a range of numbers.

Heteroaryl moieties as defined herein have C or N bonding hands. For example, in some embodiments, a ring N atom from the heteroaryl is the bonding atom to —C(O) to form an amide, carbamate, or urea. In exemplary embodiments, "heteroaryl" refers to a cyclic hydrocarbon as described above containing 5 or 6 ring atoms (i.e., C5-C6 heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "substituted" in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "salts" as used herein embraces pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. *Handbook of Pharmaceutical Salts: Properties, Selection and Use*; Verlag Helvetica Chimica Acta/Wiley-VCH: Zurich, 2002, the contents of which are hereby incorporated by reference in their entirety. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

The terms "administer," "administering, or "administration" as used herein refer to either directly administering a compound or pharmaceutically acceptable salt of the compound or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The terms "isolated" and "purified" as used herein refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the term "subject" includes, without limitation, a human or an animal. Exemplary animals include, but are not limited to, mammals such as mouse, rat, guinea pig, dog, cat, horse, cow, pig, monkey, chimpanzee, baboon, or rhesus monkey.

The term "treating" as used herein with regard to a subject, refers to improving at least one symptom of the subject's disorder. Treating can be curing, improving, or at least partially ameliorating the disorder.

Structural, chemical and stereochemical definitions are broadly taken from IUPAC recommendations, and more specifically from Glossary of Terms used in Physical Organic Chemistry (IUPAC Recommendations 1994) as summarized by Müller, P. *Pure Appl. Chem.* 1994, 66, pp. 1077-1184 and Basic Terminology of Stereochemistry (IUPAC Recommendations 1996) as summarized by Moss, G. P. *Pure Appl. Chem.* 1996, 68, pp. 2193-2222.

Atropisomers are defined as a subclass of conformers which can be isolated as separate chemical species and which arise from restricted rotation about a single bond.

Regioisomers or structural isomers are defined as isomers involving the same atoms in different arrangements.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties, and by some differences in chemical behavior towards achiral as well as chiral reagents.

The term "tautomer" as used herein refers to compounds produced by the phenomenon wherein a proton of one atom of a molecule shifts to another atom. See March, Advanced Organic Chemistry: Reactions, Mechanisms and Structures, 4th Ed., John Wiley & Sons, pp. 69-74 (1992). Tautomerism is defined as isomerism of the general form

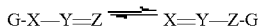

where the isomers (called tautomers) are readily interconvertible; the atoms connecting the groups X, Y and Z are typically any of C, H, O, or S, and G is a group which becomes an electrofuge or nucleofuge during isomerization. The most common case, when the electrofuge is $H^+$, is also known as "prototropy." Tautomers are defined as isomers that arise from tautomerism, independent of whether the isomers are isolable.

ChemDraw version 8.0 or 10, (CambridgeSoft Corporation, Cambridge, Mass.) was used to name structures.

The following abbreviations are used in this disclosure and have the following definitions: AcOH is acetic acid, ADP is adenosine diphosphate, ATP is adenosine triphosphate, DCM is dichloromethane, DIEA is N,N-diisopropylethylamine, DMA is N,N-dimethylacetamide, DMEM is Dulbecco's Modified Eagle Media, DMF is N,N-dimethylformamide, DMSO is dimethylsulfoxide, DTT is dithiothreitol, ESI is electrospray ionization, EtOH is ethanol, EtOAc is ethyl acetate, $Et_2O$ is diethylether, GST is glutathione S-transferase, "h" is hour or hours, Hex is hexanes, $IC_{50}$ is half maximal inhibitory concentration, min is minutes, MeCN is acetonitrile, MeOH is methanol, MS is mass spectrometry, MTBE is methyl tert-butyl ether, NADH is nicotinamide adenine dinucleotide, NMR is nuclear magnetic resonance, PBS is phosphate buffered saline, RT is room temperature, TBTU is O-(Benzotriazol-1-yl)-N,N,N',N'-tetramethyluronium tetrafluoroborate, TFA is trifluoroacetic acid, THF is tetrahydrofuran, and Tris is tris(hydroxymethyl)aminomethane.

Methods of Making

The compounds of the invention are available by the general synthetic methods illustrated in the Schemes below and the accompanying examples. Suitable reaction conditions for the steps of these schemes are well known in the art and appropriate substitutions of solvents and co-reagents are within the skill of the art. Furthermore, it will be appreciated by those skilled in the art that synthetic intermediates may be isolated and/or purified by various well known techniques as needed or desired, and that frequently, it will be possible to use various intermediates directly in subsequent synthetic steps with little or no purification. The ordinary skilled artisan will appreciate that in some circumstances, the order in which moieties are introduced is not critical. The particular order of steps required to produce the compounds of Formula I is dependent upon the particular compound being synthesized, the starting compound, and the relative liability of the substituted moieties, as is well appreciated by the ordinary skilled chemist. All substituents, unless otherwise indicated, are as previously defined, and all reagents are well known and appreciated in the art.

Compounds 1 of the invention are assembled in a step-wise manner as illustrated in Scheme 1. Acids of formula 2 are reacted with amines of formula 3 in the presence of standard peptide coupling reagents familiar to those skilled in the art to prepare amides of formula 1. Suitable reagents for the conversion of 2 to 1 include TBTU (O-(benzotriazol-1-yl)-N,N,N',N'-tetramethyluronium tetrafluoroborate), PyBOP (benzotriazol-1-yloxy)tripyrrolidinophosphonium hexafluorophosphate), EDC (1-ethyl-3-(3-dimethylaminopropyl) carbodiimide hydrochloride) and BOP-Cl (bis(2-oxo-3-oxazolidinyl)phosphonic chloride). It is recognized that in this case and in others to follow, a carboxylic acid moiety, such as found in 2, can also be activated as an acid halide, anhydride, mixed anhydride, or as an activated ester (for example a pentafluorophenyl ester). Those skilled in the art will recognize that such activated esters can react directly with amine 3 in the absence of an added peptide coupling reagent. In the case of activated acid derivatives it will be further understood that these compounds are optionally isolated as discrete intermediates prior to their union with amines 3 to form 1. Alternatively, amides 1 can be prepared via a two-step procedure wherein acids 2 are first reacted with amines 4 (L is halogen) in an analogous manner to above to afford intermediate amides 5. Reaction of 5 with an organometallic reagent M-W (6) in the presence of a palladium catalyst, for example $Pd(PPh_3)_4$, provides desired final compounds 1. The M-group of M-W 6 represents a "metallic" functionality known to undergo palladium-catalyzed reactions with aryl halides. Examples of M-groups include boronic acids or esters, trifluoroborates, tin, copper, zinc, magnesium and lithium. These M-W reagents (6), when not commercially available, are generally prepared from analogous halides by methods familiar to those skilled in the art. Using similar conditions, acids of formula 7 also are, in some embodiments, coupled with amine 3 (or amines 4 via a two-step procedure) to yield amides 8, additional compounds of the invention.

Scheme 1

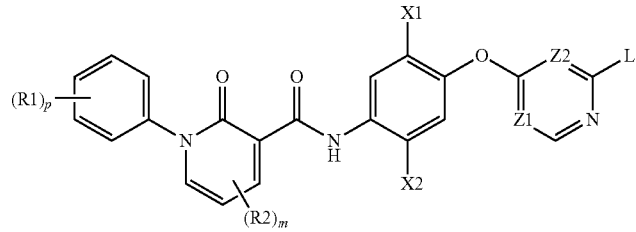

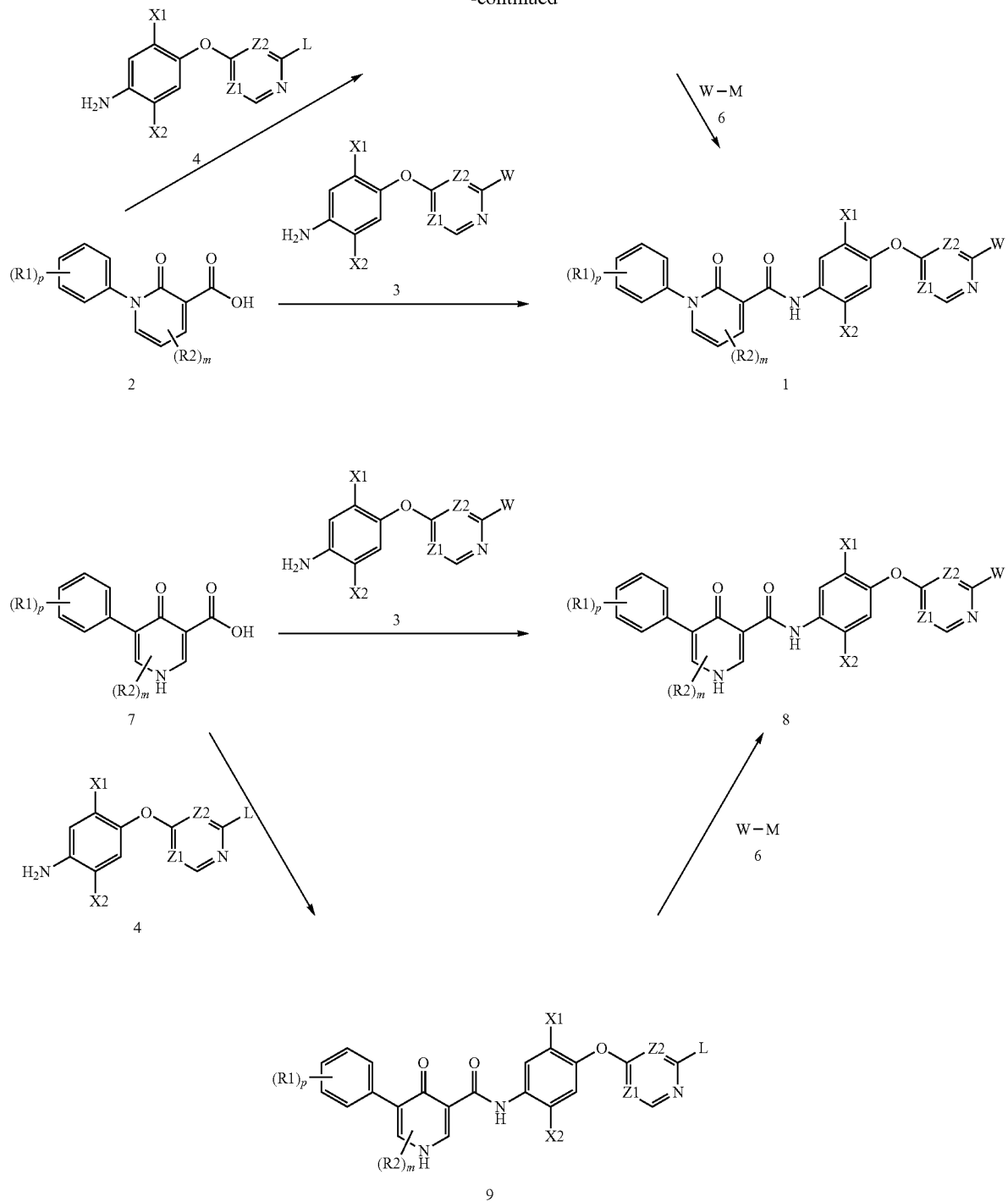

Amines 3 useful for the invention are synthesized according to methods commonly known to those skilled in the art. Scheme 2 illustrates a general method for the preparation of amines 3 which contain a central ether moiety. In general terms these are prepared by the reaction of hydroxy-heteroarenes of formula 11 with 4-fluoronitrobenzenes 10 to provide ether 12, which in turn is reduced to general amines of formula 4 by standard reducing conditions, for example, by hydrogenation, by reduction with zinc metal or by reduction with stannous chloride. Conditions for the union of 10 and 11 include the use of a base, for example cesium carbonate or sodium hydride in a polar aprotic solvent such as dimethylformamide or dimethylsulfoxide with optional heating or microwave heating. Those skilled in the art will recognize that the hydroxy-heteroarene 11 also exists in a tautomeric state found as a pyridone or pyrimidinone, the tautomeric structures of which are implicitly contained within formula 11. Compound 4 is then converted to aniline 3 via reaction with an organometallic reagent W-M (6) as described above. In one embodiment, amines 3 are prepared from 16 by reduction of the nitro moiety. Compound 16 is prepared from the reaction of 12 with W-M (6).

Scheme 2

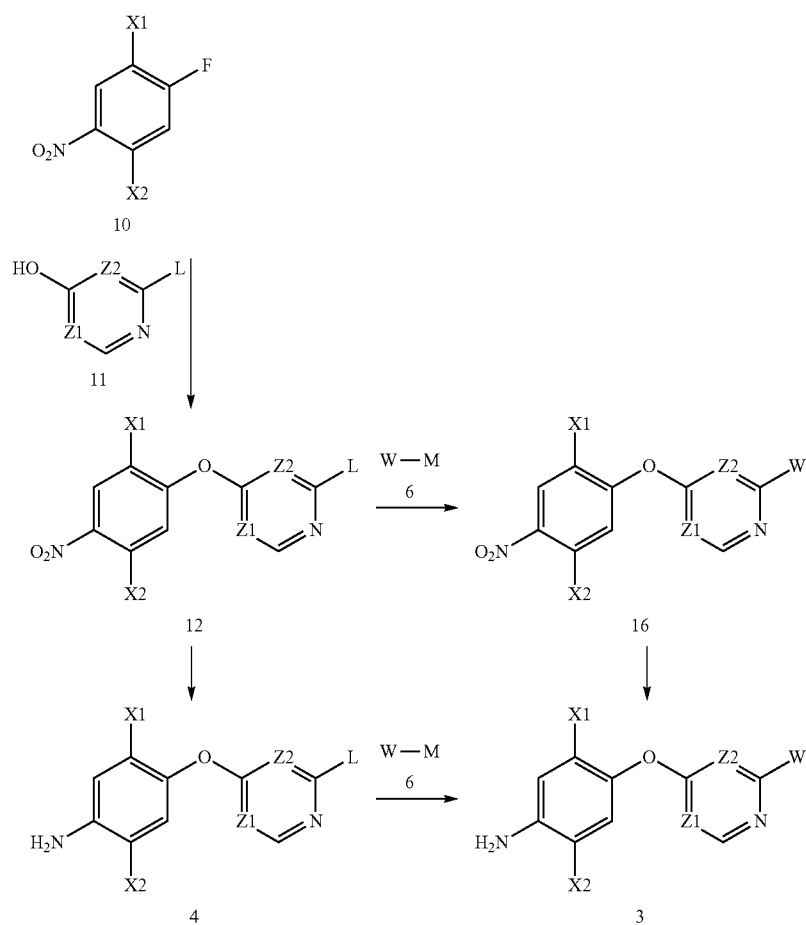

Alternative general syntheses of ethers of formula 4 are shown in Scheme 3. Reaction of amino-phenol 14 or nitro-phenol 13 with a pyridine or pyrimidine of general formula 15, provides 4 or 12 respectively. The LG-moiety of 15 represents a leaving group such as a halide or sulfonate that is displaced in a nucleophilic aromatic substitution reaction and the L-moiety of 15 is halogen. The nucleophilic substitution reaction involving compound 15 is typically performed in an aprotic solvent at temperatures ranging from ambient temp to 200° C., optionally with microwave heating. Additional conditions for the conversion of 13 to 12 or 14 to 4 include the addition of a base, for example potassium tert-butoxide or sodium hydride. In some embodiments, the conversion of nitro-phenol 13 to ether 12 is performed in the presence of an acid, for example by treatment with HCl while heating in chlorobenzene. In some embodiments, the union of 13 or 14 with 15 is catalyzed by transition metals, for example copper (Ullmann coupling) or palladium (Buchwald-Hartwig coupling). In certain embodiments, ethers of formula 12 can also be prepared by nitration of compounds of formula 18. Ethers of formula 18 are prepared using the conditions of Scheme 3 by the reaction of phenols of formula 17 with pyridine or pyrimidine of general formula 15. As indicated above, intermediate 12 is converted to amine 4 by standard reducing conditions.

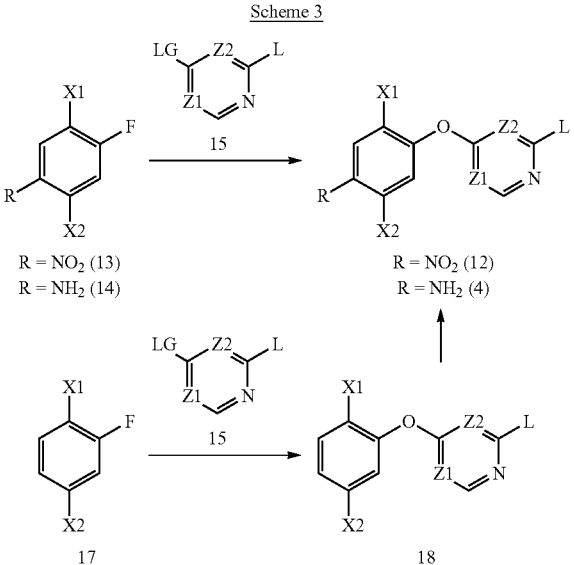

General acids 2 are prepared as indicated in Scheme 4. In one embodiment, general acids 2 are prepared from pyranones of formula 19 by the sequence shown in Scheme 4.

Thus, treatment of 19 (R is alkyl) with aniline 20 followed by cyclodehydration of the initial adduct (not shown) provides N-aryl pyridone esters of formula 21. Subsequent hydrolysis of 21 provides acid 2.

When not commercially available, acid chlorides 29 are readily prepared from the corresponding acids by treatment with thionyl chloride. Saponification of ester 30 provides acid 31, an example of general amine 7. Further treatment of 30 with alkyl halide 32 in the presence of a base, for example potassium carbonate, provides the R2-substituted pyridone ester 33. Saponification of ester 63 affords acid 34, a further example of general acid 7.

Scheme 4

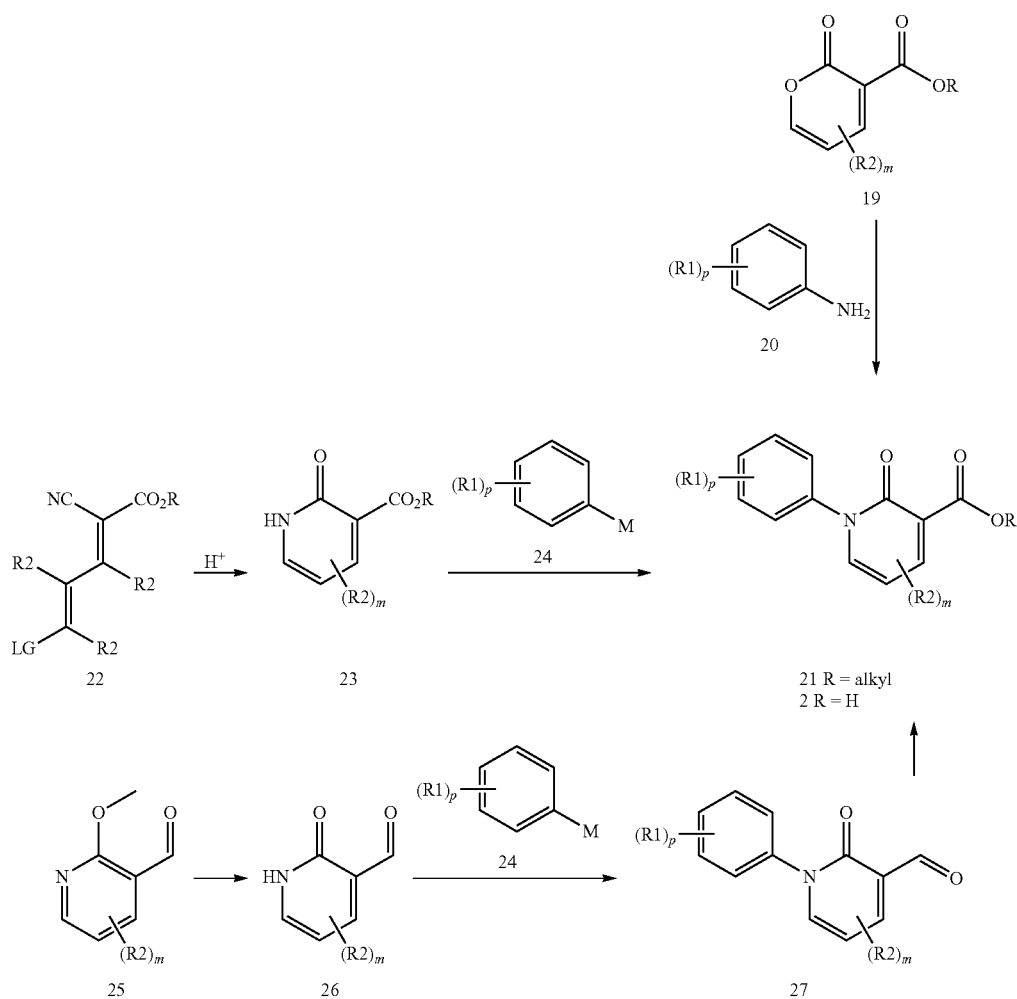

In another embodiment of Scheme 4, pyridones 21 are prepared from acyclic starting material 22 (wherein R is alkyl). The LG group of 22 is a leaving group, for example an alkoxy, dialkylamino or halo moiety. The R2 moieties in 22 are independently variable, such that they are the same or different from one another. In some embodiments, R2 is hydrogen. Heating 22 in the presence of acid, for example acetic acid, affords cyclized intermediate 23 which is then reacted with arene 24, in the presence of a copper promoter, to afford ester 21. Suitable "M" moieties for arene 24 include boronic acids (M=B(OH)$_2$) or iodides (M=iodo). In another embodiment, acid 2 can be obtained using the methods of *J. Med. Chem.* (2009) 52, pp 1251-1254. Methoxy pyridine 25 is first demethylated, for example by treatment with iodotrimethylsilane, to afford 26. Reaction of 26 with arene 24 as described above provides N-aryl pyridone 27 which in turn is oxidized to acid 2.

Scheme 5 illustrates the preparation of acids 31 and 34, examples of general acid 7. Using methods described in *J. Med. Chem.* (2008) 51, pp 5330-5341, Meldrum's acid (28) and acid chloride 29 are combined to yield pyridone ester 30.

Scheme 5

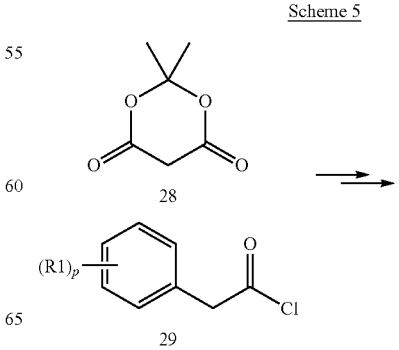

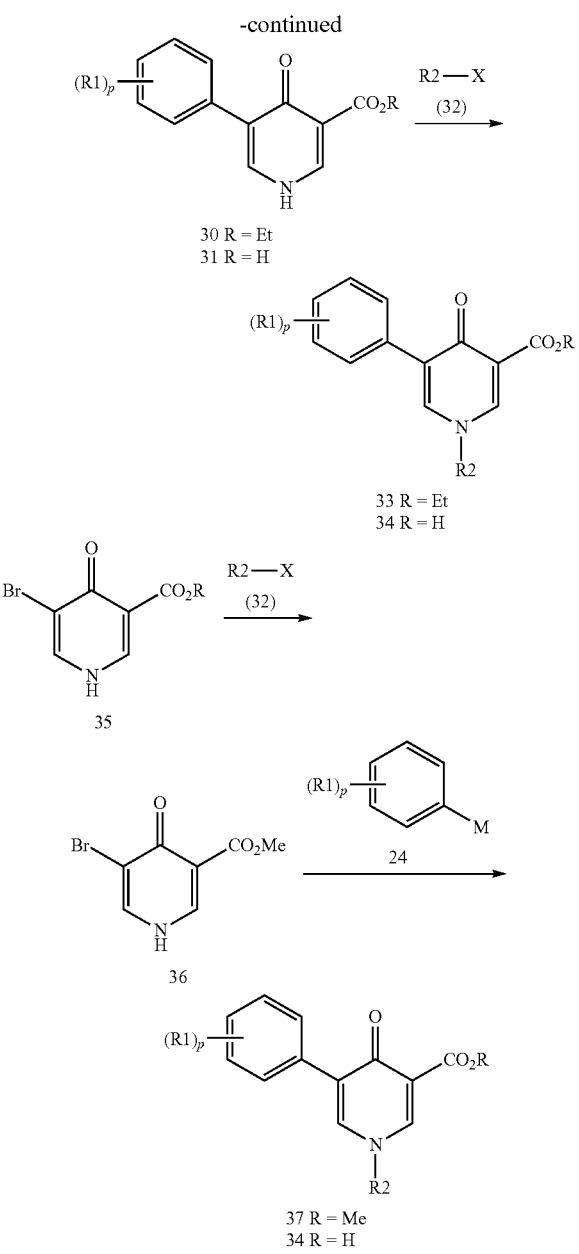

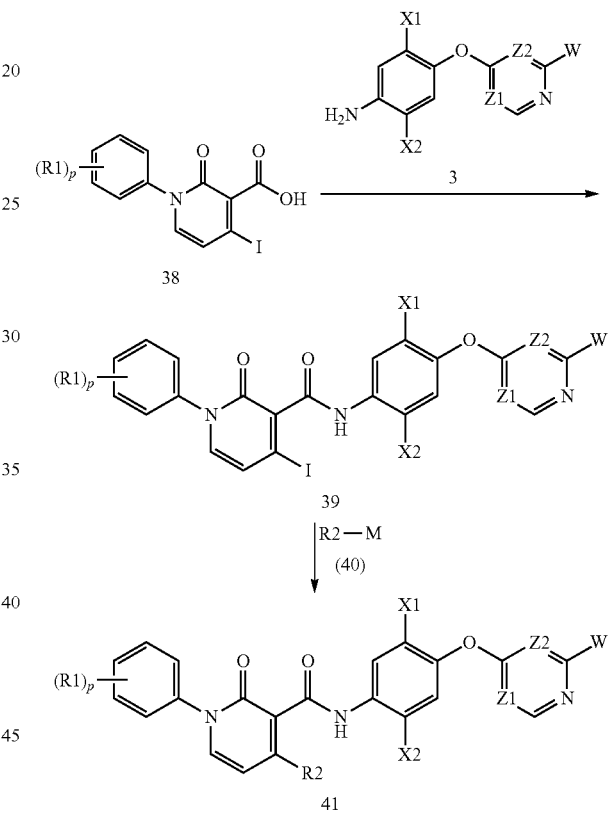

reagent 40 is an amine (wherein M is $NH_2$). In the instance in which R2 is cyano, reagent 40 represents a metal cyanide (wherein M is Cu or Zn) that replaces the iodine atom of 39, in some embodiments in the presence of a transition metal, for example palladium. In the instance in which R2 is alkyl, the "M" moiety of 40 represents a "metallic" functionality known to undergo palladium-catalyzed reactions with aryl halides. Examples of M-groups include boronic acids or esters, trifluoroborates, tin, copper, zinc, magnesium and lithium. Those skilled in the art will recognize that in certain instances, an alkyl R2 is introduced as a vinylic or acetylenic moiety that is subsequently converted to an alkyl moiety by standard reducing conditions such as hydrogenation over a transition metal catalyst.

An additional synthesis of acid 34 is also illustrated in Scheme 5 commencing with bromide 35 (see *J. Med. Chem.* (2008) 51, pp 5330-5341). Thus, alkylation of 35 with 32, as described above, provides 36. Treatment of 36 with arene 24 (M is boronic acid or boronate) in the presence of a palladium catalyst and a base provides pyridone ester 37. Saponification of ester 37 provides acid 34.

Other compounds of general formula 1 can be obtained via the synthesis described in Scheme 6. Carboxylic acid 38 (an acid of general formula 21 wherein R2 is I) is converted to amide 39 via reaction with amine 3 utilizing either a peptide coupling reagent or through conversion of the acid moiety to an acid chloride (as described in Scheme 1). Replacement of the iodide with another R2 moiety by reaction of 39 with 40 provides compound 41, an example of formula 1. In the instance in which R2 is an alkoxy moiety, reagent 40 represents an alcohol (wherein M is H) or an alkoxide (wherein M is alkali) that displaces the iodide to form a carbon-oxygen bond. In the instance in which R2 is an amino group, then Using the synthetic procedures and methods described herein and methods known to those skilled in the art, the following compounds were made: N-(2,5-difluoro-4-((2-(1-methyl-1H-pyrazol-4-yl)pyridin-4-yl)oxy)phenyl)-1-(4-fluorophenyl)-2-oxo-1,2-dihydropyridine-3-carboxamide, N-(2,5-difluoro-4-(2-(1-methyl-1H-pyrazol-4-yl)pyridin-4-yloxy)phenyl)-4-ethoxy-1-(4-fluorophenyl)-2-oxo-1,2-dihydropyridine-3-carboxamide, N-(2,5-difluoro-4-((2-(1-(2-hydroxyethyl)-1H-pyrazol-4-yl)pyridin-4-yl)oxy)phenyl)-1-(4-fluorophenyl)-2-oxo-1,2-dihydropyridine-3-carboxamide, N-(2,5-difluoro-4-((2-(1-methyl-1H-pyrazol-4-yl)pyridin-4-yl)oxy)phenyl)-1-(4-fluorophenyl)-4-(methylamino)-2-oxo-1,2-dihydropyridine-3-carboxamide, N-(2,5-difluoro-4-((2-(1-methyl-1H-pyrazol-4-yl)pyridin-4-yl)oxy)phenyl)-4-(ethylamino)-1-(4-fluorophenyl)-2-oxo-1,2-dihydropyridine-3-carboxamide, N-(2,5-difluoro-4-((2-(1-isopropyl-1H-pyrazol-4-yl)pyridin-4-yl)oxy)phenyl)-4-ethoxy-1-(4-fluorophenyl)-2-oxo-1,2-dihydropyridine-3-carboxamide, 4-ethoxy-N-(4-((2-(1-ethyl-1H-pyrazol-4-yl)

pyridin-4-yl)oxy)-2,5-difluorophenyl)-1-(4-fluorophenyl)-2-oxo-1,2-dihydropyridine-3-carboxamide, N-(4-((2-(1H-pyrazol-4-yl)pyridin-4-yl)oxy)-2,5-difluorophenyl)-4-ethoxy-1-(4-fluorophenyl)-2-oxo-1,2-dihydropyridine-3-carboxamide, N-(2,5-difluoro-4-((2-(1-methyl-1H-pyrazol-4-yl)pyridin-4-yl)oxy)phenyl)-5-(4-fluorophenyl)-1-methyl-4-oxo-1,4-dihydropyridine-3-carboxamide, and N-(2,5-difluoro-4-((2-(1-methyl-1H-pyrazol-4-yl)pyridin-4-yl)oxy)phenyl)-5-(4-fluorophenyl)-4-oxo-1,4-dihydropyridine-3-carboxamide.

EXAMPLES

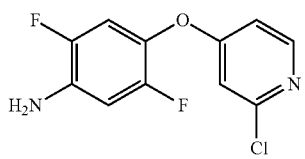 [SMILES: Nc1cc(F)c(Oc2ccnc(Cl)c2)cc1F]

Example A1

Anhydrous DMF (150 mL) was added to 60% NaH in mineral oil (2.72 g, 67.9 mmol) under an Ar atmosphere, cooled in an ice bath, treated portion-wise with a solution of 2-chloropyridin-4-ol (8 g, 61.8 mmol) in DMF (30 mL) and stirred cold for 5 minutes. The cooling bath was removed and the mixture was warmed to RT and stirred for 20 minutes. 1,2,4-Trifluoro-5-nitrobenzene (13.12 g, 74.1 mmol) was added and the reaction mixture heated at 90° C. for 3 h. The reaction mixture was cooled to RT, concentrated to dryness, treated with EtOH (50 mL) and MeOH (20 mL), warmed gently, then cooled to RT. The yellow solid was collected by filtration, rinsed with EtOH (50 mL) and hexanes (20 mL) and dried under vacuum overnight to provide 2-chloro-4-(2,5-difluoro-4-nitrophenoxy)pyridine as a yellow solid (11.68 g, 63% yield). $^1$H NMR (400 MHz, DMSO-$d_6$): δ 8.48 (dd, J=10.2, 7.0 Hz, 1H), 8.41 (d, J=5.6 Hz, 1H), 7.90 (dd, J=11.6, 6.7 Hz, 1H), 7.41 (d, J=2.1 Hz, 1H), 7.26 (dd, J=5.6, 2.4 Hz, 1H); MS (ESI): m/z 287.0 [M+H]$^+$ A solution of 2-chloro-4-(2,5-difluoro-4-nitrophenoxy)pyridine (11.68 g, 40.8 mmol) in MeOH (200 mL) was treated with Raney Ni (50% wet, 0.955 g, 8.15 mmol) and hydrogenated (10-20 psi) for 4 h. The mixture was filtered through a pad of diatomaceous earth and the filtrate was concentrated to dryness to provide 4-(2-chloropyridin-4-yloxy)-2,5-difluoroaniline (8.2 g, 72% yield). $^1$H NMR (400 MHz, DMSO-$d_6$): δ 8.28 (d, J=5.9 Hz, 1H), 7.25 (dd, J=11.2, 7.5 Hz, 1H), 7.02 (dd, J=2.2 Hz, 1H), 6.95 (dd, J=5.8, 2.0 Hz, 1H), 6.74 (dd, J=12.3, 8.3 Hz, 1H), 5.57 (s, 2H); MS (ESI): m/z 257.0 [M+H]$^+$

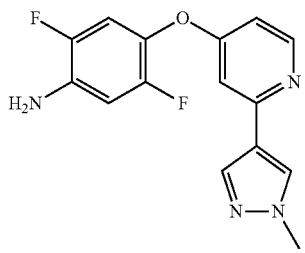 [SMILES: Cn1cc(-c2cc(Oc3cc(F)c(N)cc3F)ccn2)cn1]

Example A2

A solution of Example A1 (450 mg, 1.76 mmol) and 1-methyl-4-(4,4,5,5-tetramethyl-1,3,2-dioxaborolan-2-yl)-1H-pyrazole (400 mg, 1.9 mmol) in DMF (30 mL) was treated with tetrakis(triphenylphosphine)palladium(0) [Pd(PPh$_3$)$_4$] (105 mg, 0.09 mmol) and an aqueous solution of potassium phosphate (2 M, 1.8 mL). The mixture was flushed with nitrogen for 10 min, and then heated at 90° C. overnight. After cooling to RT, the mixture was treated with water, extracted with EtOAc (4×) and the combined organics were washed with brine, dried (Na$_2$SO$_4$), concentrated under reduced pressure and purified by silica gel chromatography to give 2,5-difluoro-4-((2-(1-methyl-1H-pyrazol-4-yl)pyridin-4-yl)oxy)aniline (335 mg, 63% yield). $^1$H NMR (300 MHz, DMSO-$d_6$): δ 8.35 (d, J=5.7 Hz, 1H), 8.27 (s, 1H), 7.98 (s, 1H), 7.24-7.18 (m, 2H), 6.75 (dd, J=12.3, 8.1 Hz, 1H), 6.62 (dd, J=5.4, 2.1 Hz, 1H), 5.53 (br s, 2H), 3.87 (s, 3H); MS (ESI): m/z 303.1 [M+1]$^+$.

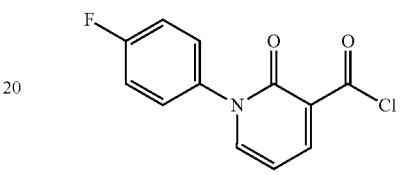

Example A3

A solution of 1-(4-fluorophenyl)-2-oxo-1,2-dihydropyridine-3-carboxylic acid (prepared according to: *J. Med. Chem.* (2008), 51, 5330-5341) (0.257 g, 1.1 mmol) in SOCl$_2$ (2.409 mL, 33.0 mmol) was heated to 60° C. for 35 min, cooled to RT and concentrated to dryness. The residue was co-evaporated with toluene (2×) to afford 1-(4-fluorophenyl)-2-oxo-1,2-dihydropyridine-3-carbonyl chloride (100% yield assumed) as a yellow solid.

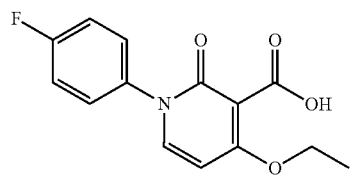 [SMILES: CCOc1ccn(-c2ccc(F)cc2)c(=O)c1C(=O)O]

Example A4

A mixture of ethyl 2-cyanoacetate (120 g, 1.06 mol) and triethylorthoacetate (354 g, 2.12 mol) in glacial acetic acid (33 g, 0.53 mol) was stirred at 120~130° C. overnight. The mixture was concentrated under vacuum to provide crude ethyl 2-cyano-3-ethoxybut-2-enoate and carried into the next reaction without further purification assuming 100% conversion.

A mixture of ethyl 2-cyano-3-ethoxybut-2-enoate (194 g theory, 1.06 mol) and N,N-dimethylformamide dimethyl acetal (160 g, 1.325 mol) was heated at 70° C. for 2 h. The mixture was concentrated under high vacuum to provide crude ethyl 2-cyano-5-(dimethylamino)-3-ethoxypenta-2,4-dienoate which was used directly without further purification.

A mixture of ethyl 2-cyano-5-(dimethylamino)-3-ethoxypenta-2,4-dienoate (150 g, 0.63 mol) and HOAc (600 mL) was refluxed overnight. The mixture was cooled to RT, concentrated to dryness, treated with water and washed with EtOAc (2×). The aqueous layer was made basic (pH=9-10) with NaHCO$_3$, extracted with DCM (3×) and the combined organics were washed with brine, dried over Na$_2$SO$_4$, concentrated and purified by silica gel chromatography to afford ethyl 4-ethoxy-2-oxo-1,2-dihydropyridine-3-carboxylate (90 g, 67% yield).

A mixture of ethyl 4-ethoxy-2-oxo-1,2-dihydropyridine-3-carboxylate (60 g, 0.284 mol), 4-fluoro phenylboronic acid (120 g, 0.853 mol), Cu(AcO)$_2$ (113 g, 0.568 mol) and pyridine (88 g, 1.137 mol) in DCM (500 mL) was stirred at RT for 4 h open to air. The solids were removed via filtration, washed with water and the filtrate extracted with DCM (2×). The combined organics were dried over Na$_2$SO$_4$ and concentrated to afford ethyl 4-ethoxy-1-(4-fluorophenyl)-2-oxo-1,2-dihydropyridine-3-carboxylate. The product was carried forward without further purification. (77 g, 95% yield).

A mixture of ethyl 4-ethoxy-1-(4-fluorophenyl)-2-oxo-1,2-dihydropyridine-3-carboxylate (60 g, 0.196 mol) and LiOH (30 g, 0.6 mol) in EtOH (200 mL) and water (100 mL) was stirred at RT for 16 h. The mixture was concentrated to remove EtOH, the aqueous residue diluted with additional water (300 mL), washed with EtOAc (1×) and acidified to pH<2 with conc. HCl. The mixture was extracted with EtOAc (3×) and the combined organics were washed with brine, dried over Na$_2$SO$_4$ and concentrated to dryness. The residue was treated with pet ether and the resulting solid collected via filtration to afford 4-ethoxy-1-(4-fluorophenyl)-2-oxo-1,2-dihydropyridine-3-carboxylic acid (43 g, 79%). $^1$H NMR (400 MHz, DMSO-d$_6$): δ 7.95 (d, J=8.0 Hz, 1H), 7.48 (m, 2H), 7.35 (m, 2H), 6.58 (d, J=7.6 Hz, 1H), 4.28 (q, J=7.2 Hz, 2H), 1.32 (t, J=7.2 Hz, 3H).

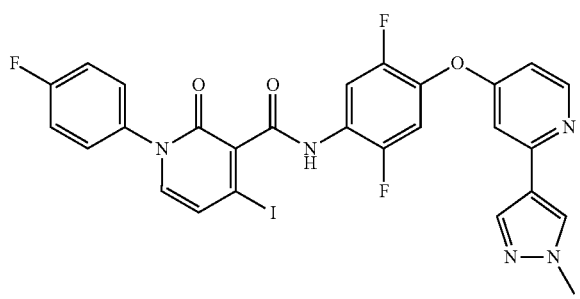 [SMILES: Cn1cc(-c2cc(Oc3cc(F)c(NC(=O)c4c(I)ccn(-c5ccc(F)cc5)c4=O)cc3F)ccn2)cn1]

Example A5

A −78° C. solution of 2-methoxypyridine (40 g, 0.37 mol) in THF (1 L) was treated with t-BuLi (163 mL, 0.41 mol), stirred at −78° C. for 0.5 h, treated with N-(2-dimethylaminoethyl)-N-methylformamidine (52.9 g, 0.41 mol) over 10 min, stirred at −78° C. for another 0.5 h, then warmed to −20° C. for 45 minutes. The mixture was cooled to −40° C., treated with n-BuLi (289 mL, 0.46 mol), stirred at −40° C. for 1.5 h, then cooled to −78° C. The cold mixture was added via syringe to a solution of I$_2$ (187.8 g, 0.74 mol) in THF at −78° C., stirred at −78° C. for 0.5 h, then warmed to 0° C. The mixture was quenched with satd. NaS$_2$O$_3$, the organic layer washed with brine, dried over Na$_2$SO$_4$, concentrated under reduce pressure, and purified by chromatography. The resulting solid was washed with pet ether to afford 4-iodo-2-methoxynicotinaldehyde (22 g, 23%). $^1$H NMR (400 MHz, CDCl$_3$): δ 10.20 (s, 1H), 7.84 (d, J=5.6 Hz, 1H), 7.53 (d, J=5.2 Hz, 1H), 3.99 (s, 3H).

A mixture of 4-iodo-2-methoxynicotinaldehyde (25 g, 83 mmol) and sodium iodide (37.0 g, 249 mmol) in MeCN (500 mL) was treated drop-wise with chlorotrimethylsilane (31.4 mL, 249 mmol) over 15 minutes. The reaction mixture was stirred at RT for 2 h, then to dryness. The residue was suspended in EtOAc, water, and satd. NaHCO$_3$, the solid collected via filtration, triturated with MeCN and dried to afford 4-iodo-2-oxo-1,2-dihydropyridine-3-carbaldehyde (12 g, 51%) as a yellow solid. MS (ESI) m/z: 250.0 (M+H$^+$).

A mixture of 4-iodo-2-oxo-1,2-dihydropyridine-3-carbaldehyde (12.0 g, 48.3 mmol), 4-fluorophenylboronic acid (20.1 g, 144.7 mmol), copper(II) acetate (17.55 g, 96.75 mmol), and myristic acid (44 g, 193 mmol) in toluene (700 mL) was treated with 2,6-lutidine (45 mL, 385.5 mmol) and stirred vigorously at RT for 1 day. Additional 4-fluorophenylboronic acid (5 g) was added and the reaction was stirred vigorously for an additional 3 days. The reaction mixture was concentrated to dryness, suspended in 10% MeOH/EtOAc and the solids removed via filtration through diatomaceous earth. The filtrate was concentrated to dryness, the residue treated with EtOAc and water and again filtered through diatomaceous earth. The filtrate was washed with 1N HCl, dried over Na$_2$SO$_4$ and concentrated to dryness. The material was treated with EtOAc and the resulting solid was collected via filtration to afford 1-(4-fluorophenyl)-4-iodo-2-oxo-1,2-dihydropyridine-3-carbaldehyde (8.0 g, 42%) as a yellow solid.

A 0° C. mixture of 1-(4-fluorophenyl)-4-iodo-2-oxo-1,2-dihydropyridine-3-carbaldehyde (8 g, 23 mmol) and sodium phosphate monobasic (8 g, 58.4 mmol) in 1:1:1 THF/t-BuOH/water (105 mL) was treated with 2-methyl-2-butene (2.0 M in THF, 36.1 mL, 72.2 mmol) followed by sodium chlorite (4.8 g, 53.7 mmol) and the vigorously stirred mixture warmed to RT and stirred for 1 h. HCl (1 M, 20 mL) was added, the mixture stirred for 5 minutes and the solid was collected via filtration and washed with water, EtOAc, then Et2O. The layers of the filtrate were separated and the aqueous layer extracted with additional EtOAc. The combined organics were dried over MgSO$_4$, concentrated to dryness, the residue suspended in EtOAc, the solid collected via filtration and combined with the above-isolated solid. The combined material was dissolved in a minimum amount of 1N NaOH, treated with EtOAc, stirred vigorously for 5 minutes and the layers separated. The aqueous layer was washed with EtOAc, acidified to pH=1 with conc. HCl and the resulting solid was collected via filtration, washed with water, EtOAc and Et2O and dried to afford 1-(4-fluorophenyl)-4-iodo-2-oxo-1,2-dihydropyridine-3-carboxylic acid (5.4 g, 65%). $^1$H NMR (400 MHz, DMSO-d$_6$): δ 13.5 (brs, 1H), 7.43-7.47 (m, 3H), 7.30-7.35 (m, 2H), 6.76 (d, J=7.2 Hz, 1H).

A mixture of 1-(4-fluorophenyl)-4-iodo-2-oxo-1,2-dihydropyridine-3-carboxylic acid (200 mg, 0.557 mmol), SOCl$_2$ (330 mg, 2.78 mmol) and one drop of DMF in toluene (30 mL) was refluxed for 2 h. The mixture was concentrated under vacuum to afford crude 1-(4-fluoro-phenyl)-4-iodo-2-oxo-1,2-dihydro-pyridine-3-carbonyl chloride (200 mg, 95%).

A mixture of 1-(4-fuoro-phenyl)-4-iodo-2-oxo-1,2-dihydro-pyridine-3-carbonyl chloride (200 mg, 0.53 mmol), Example A2 (160 mg, 0.53 mmol) and DIEA (137 mg, 1.06 mmol) in THF (10 mL) was stirred at RT overnight. The mixture was concentrated to afford crude 1-(4-fluoro-phenyl)-4-iodo-2-oxo-1,2-dihydro-pyridine-3-carboxylic acid {2,5-difluoro-4-[2-(1-methyl-1H-pyrazol-4-yl)-pyridin-4-yloxy]-phenyl}-amide (208 mg, 81%), which was carried on without further purification.

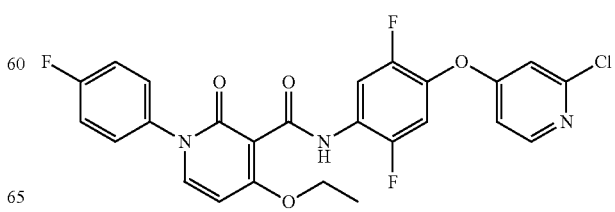

Example A6

A solution of Example A4 (1.188 g, 4.29 mmol) in SOCl$_2$ (5 mL) was heated at 60° C. for 1 h. The mixture was concentrated to dryness, then co-evaporated with toluene to afford crude 4-ethoxy-1-(4-fluorophenyl)-2-oxo-1,2-dihydropyridine-3-carbonyl chloride. The residue was dissolved in DCM (25 mL), treated sequentially with Et$_3$N (986 mg, 9.74 mmol), Example A1 (1.0 g, 3.90 mmol) and catalytic pyridine (31 mg, 0.390 mmol) and stirred at RT for 2 h. Additional 4-ethoxy-1-(4-fluorophenyl)-2-oxo-1,2-dihydropyridine-3-carbonyl chloride (746 mg, 2.52 mmol) (prepared as above) was added and stirred at RT for 1 h. The mixture was washed with H$_2$O, then brine, dried over Na$_2$SO$_4$ and concentrated to dryness. The resulting material was triturated with EtOAc, the solid collected via filtration and dried. The filtrate was concentrated to dryness, purified via silica gel chromatography (EtOAc/Hex) and combined with the above solid to afford N-(4-((2-chloropyridin-4-yl)oxy)-2,5-difluorophenyl)-4-ethoxy-1-(4-fluorophenyl)-2-oxo-1,2-dihydropyridine-3-carboxamide (1.585 g, 79%) as a tan solid. MS (ESI) m/z: 516.1 (M+H$^+$).

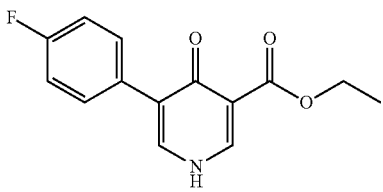 [SMILES: CCOC(=O)c1c[nH]cc(-c2ccc(F)cc2)c1=O]

Example A7

A mixture of 4-fluorophenylacetyl chloride (4.91 g, 24.3 mmol), 2,2-dimethyl-1,3-dioxane-4,6-dione (3.50 g, 24.3 mmol) and DIEA (5.84 g, 49.8 mmol) in DCM (30 mL) was stirred for 1 h at 0° C., then warmed to RT for 2 h. The solution was diluted with DCM, washed with 0.1 N HCl and brine, dried over Na$_2$SO$_4$ and evaporated to dryness. The resulting orange solid was suspended in EtOH (100 mL) and refluxed for 2 hours. The solution was evaporated and the resulting orange oil was left in the freezer overnight to give a yellow solid. The crude solid was recrystallized from EtOH to afford ethyl 4-(4-fluorophenyl)-3-oxobutanoate (5.3 g, 86.8% yield).

A mixture of ethyl 4-(4-fluorophenyl)-3-oxobutanoate (5.3 g, 21.1 mmol), and DMF-dimethylacetal (7.53 g, 63.3 mmol) in toluene (50 mL) was heated at reflux with removal of the MeOH for 2 h and was then concentrated under vacuum. The residue was dissolved in MeOH (50 mL), treated with NH$_4$OAc (8.1 g, 105.5 mmol) and the mixture was refluxed for 1.5 h. The precipitate was collected by filtration and successively washed with MeOH, water, then MeOH again to give ethyl 5-(4-fluorophenyl)-4-oxo-1,4-dihydropyridine-3-carboxylate (3.3 g, 60% yield). $^1$H-NMR (400 MHz, CD$_3$OD): δ 9.19 (d, J=0.8 Hz, 1H), 8.81 (d, J=0.8 Hz, 1H), 7.74 (dd, J=8.8, 5.2 Hz, 2H), 7.29 (t, J=8.8 Hz, 2H), 4.60 (q, J=7.2 Hz, 2H), 1.49 (t, J=7.2 Hz, 3H) [NH not visible]; MS (ESI) m/z: 261.9 (M+H$^+$).

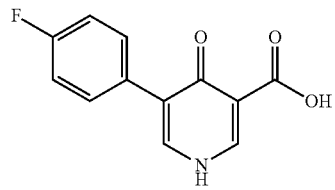 [SMILES: O=C(O)c1c[nH]cc(-c2ccc(F)cc2)c1=O]

Example A8

A suspension of Example A7 (0.750 g, 2.87 mmol) in 3M NaOH (7.5 mL, 22.50 mmol) was heated at 100° C. for 1.5 h. The mixture was cooled to RT, acidified to pH 2 with 3M HCl and the resulting solid was collected via filtration and dried to afford 5-(4-fluorophenyl)-4-oxo-1,4-dihydropyridine-3-carboxylic acid (669 mg, 100%) as a white solid. MS (ESI) m/z: 234.1 (M+H$^+$).

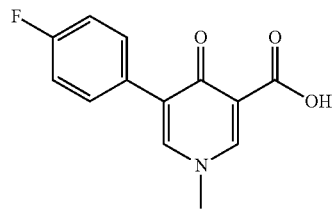 [SMILES: Cn1cc(C(=O)O)c(=O)c(-c2ccc(F)cc2)c1]

Example A9

A mixture of Example A7 (1.5 g, 5.7 mmol) and iodomethane (0.9 g, 6.3 mmol) in satd. NaHCO$_3$ (25 mL) was heated at 60° C. overnight. The mixture was filtered. The solid was concentrated under vacuum to afford ethyl 5-(4-fluorophenyl)-1-methyl-4-oxo-1,4-dihydropyridine-3-carboxylate (1.1 g, 69.9% yield) which was used without further purification.

A mixture of ethyl 5-(4-fluorophenyl)-1-methyl-4-oxo-1,4-dihydropyridine-3-carboxylate (1.1 g, 4 mmol) and NaOH (1.6 g, 40 mmol) in water (25 mL) was stirred at RT overnight. The mixture was washed with EtOAc (2×) and the aqueous layer was acidified to pH=1-2 with conc. HCl. The resulting precipitate was collected by filtration and dried under vacuum to afford 5-(4-fluorophenyl)-1-methyl-4-oxo-1,4-dihydropyridine-3-carboxylic acid (810 mg, 81.9% yield). $^1$H-NMR (400 MHz, CDCl$_3$): δ 15.76 (s, 1H), 8.49 (d, J=2.4 Hz, 1H), 7.58 (m, 3H), 7.14 (t, J=8.8 Hz, 2H), 3.92 (s, 3H).

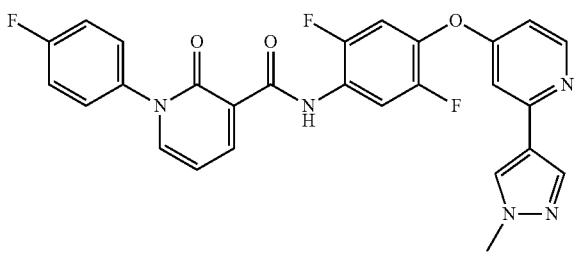 [SMILES: Cn1cc(-c2cc(Oc3cc(F)c(NC(=O)c4cccn(-c5ccc(F)cc5)c4=O)cc3F)ccn2)cn1]

Example 1

A mixture of Example A2 (0.324, 1.073 mmol) and K$_2$CO$_3$ (0.178 g, 1.288 mmol) in EtOAc (1.4 mL) and H$_2$O (2.15 mL) was stirred vigorously for 5 min, treated with a solution of Example A3 (0.108 g, 0.429 mmol) in EtOAc (1.4 mL) and stirred at RT for 2 h. The layers were separated, the aqueous layer extracted with DCM and the combined organics were dried over Na₂SO₄ and concentrated to dryness. The residue was combined with K₂CO₃ (0.265 g, 1.920 mmol) in DCM (1.4 mL) and H₂O (2.1 mL), stirred vigorously for 5 min, treated with a solution of Example A3 (0.403 g, 1.60 mmol) in DCM (1.4 mL) and stirred at RT overnight. The layers were separated, the aqueous layer extracted with DCM and the combined organics were dried over Na₂SO₄, concentrated to dryness and purified via silica gel chromatography (MeOH/DCM) to afford N-(2,5-difluoro-4-((2-(1-methyl-1H-pyrazol-4-yl)pyridin-4-yl)oxy)phenyl)-1-(4-fluorophenyl)-2-oxo-1,2-dihydropyridine-3-carboxamide (400 mg, 72%) as a pale yellow solid. ¹H NMR (400 MHz, DMSO-d₆): δ 12.43 (s, 1H), 8.60 (dd, J=7.3, 2.2 Hz, 1H), 8.55 (dd, J=12.6, 7.2 Hz, 1H), 8.37 (d, J=5.7 Hz, 1H), 8.27 (s, 1H), 8.15 (dd, J=6.6, 2.2 Hz, 1H), 7.97 (s, 1H), 7.62-7.56 (m, 3H), 7.41 (m, 2H), 7.25 (d, J=2.4 Hz, 1H), 6.76-6.71 (m, 2H), 3.84 (s, 3H); MS (ESI) m/z: 518.1 (M+H⁺).

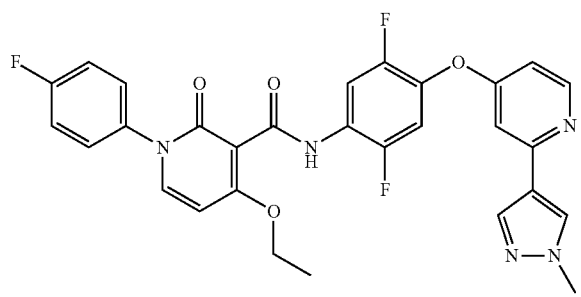 [SMILES: CCOc1ccn(-c2ccc(F)cc2)c(=O)c1C(=O)Nc1cc(F)c(Oc2ccnc(-c3cnn(C)c3)c2)cc1F]

Example 2

Method 1

To a suspension of Example A4 (0.400 g, 1.443 mmol) in DCM (10 mL) was added Example A2 (0.300 g, 0.992 mmol) and diethylchlorophosphate (0.171 g, 0.992 mmol) followed by Et₃N (0.201 g, 1.985 mmol). The resulting mixture was stirred at RT overnight. The solvent was concentrated to dryness and purified via silica gel chromatography (EtOAc/Hex). The material was treated with MeOH, the solid collected via filtration and dried to afford N-(2,5-difluoro-4-(2-(1-methyl-1H-pyrazol-4-yl)pyridin-4-yloxy)phenyl)-4-ethoxy-1-(4-fluorophenyl)-2-oxo-1,2-dihydropyridine-3-carboxamide (220 mg 39%) as a white solid. ¹H NMR (400 MHz, DMSO-d₆): δ 11.21 (s, 1H), 8.39-8.32 (m, 2H), 8.27 (s, 1H), 7.98 (s, 1H), 7.92 (d, J=7.8 Hz, 1H), 7.54-7.46 (m, 3H), 7.36 (m, 2H), 7.25 (d, J=2.4 Hz, 1H), 6.72 (dd, J=5.7, 2.4 Hz, 1H), 6.55 (d, J=7.9 Hz, 1H), 4.28 (q, J=7.0 Hz, 2H), 3.84 (s, 3H), 1.33 (t, J=7.0 Hz, 3H); MS (ESI) m/z: 562.2 (M+H⁺).

Method 2

A suspension of Example A4 (9.00 g, 32.5 mmol) in SOCl₂ (27.00 g, 227 mmol) was heated at 70° C. for 1 h. The mixture was concentrated to dryness, co-evaporated with hexane (2×), and the residue dissolved in DCM (150 mL), treated with Example A2 (6.8 g, 22.50 mmol) and Et₃N (6.83 g, 67.5 mmol) and stirred at RT overnight. The mixture was treated with H₂O, the layers separated and the aqueous layer extracted with additional DCM (1×). The combined organics were dried over Na₂SO₄, concentrated to dryness and purified via silica gel chromatography (EtOAc/DCM). The material was re-purified via silica gel chromatography (MTBE, MeCN/MTBE, THF/MeCN), then stirred in hot MeOH, the solid collected via filtration and dried to afford N-(2,5-difluoro-4-(2-(1-methyl-1H-pyrazol-4-yl)pyridin-4-yloxy)phenyl)-4-ethoxy-1-(4-fluorophenyl)-2-oxo-1,2-dihydropyridine-3-carboxamide (4.20 g, 33%) as an off-white solid.

Example 3

A mixture of 4-(4,4,5,5-tetramethyl-1,3,2-dioxaborolan-2-yl)-1H-pyrazole (0.500 g, 2.58 mmol), (2-bromoethoxy)-t-butyldimethylsilane (2.211 mL, 10.31 mmol), K₂CO₃ (1.425 g, 10.31 mmol) and NaI (0.039 g, 0.258 mmol) in MeCN (8 mL) was heated to 70° C. for 2 days. The mixture was cooled to RT, the solid removed via filtration, rinsed with EtOAc and the filtrate washed with 50% satd. NaCl (1×). The organic layer was dried over MgSO₄, concentrated to dryness and purified via silica gel chromatography (EtOAc/Hex) to afford 1-(2-((tert-butyldimethylsilyl)oxy)ethyl)-4-(4,4,5,5-tetramethyl-1,3,2-dioxaborolan-2-yl)-1H-pyrazole (574 mg, 63%) as a colorless oil. ¹H NMR (400 MHz, DMSO-d₆): δ 7.79 (s, 1H), 7.51 (s, 1H), 4.12 (t, J=5.4 Hz, 2H), 3.79 (t, J=5.4 Hz, 2H), 1.17 (s, 12H), 0.71 (s, 9H), −0.17 (s, 6H); MS (ESI) m/z: 353.2 (M+H⁺).

A solution of Example A1 (0.147 g, 0.572 mmol) in THF (1 mL) was treated with Et₃N (0.120 mL, 0.858 mmol) and a suspension of Example A3 (0.216 g, 0.858 mmol) in THF (2 mL). The mixture was layered with argon and stirred at RT overnight. The mixture was cooled to RT, the solid removed via filtration, rinsed with THF and the filtrate concentrated to dryness. The residue was triturated with MeCN, sonicated and the resulting solid collected via filtration and dried to afford N-(4-((2-chloropyridin-4-yl)oxy)-2,5-difluorophenyl)-1-(4-fluorophenyl)-2-oxo-1,2-dihydropyridine-3-carboxamide (104 mg, 38%) as a white solid. ¹H NMR (400 MHz, DMSO-d₆): δ 12.51 (s, 1H), 8.71-8.61 (m, 2H), 8.38 (d, J=5.8 Hz, 1H), 8.23 (dd, J=6.6, 2.2 Hz, 1H), 7.69 (m, 3H), 7.49 (m, 2H), 7.25 (d, J=2.3 Hz, 1H), 7.13 (dd, J=5.8, 2.3 Hz, 1H), 6.82 (m, 1H).

A mixture of N-(4-((2-chloropyridin-4-yl)oxy)-2,5-difluorophenyl)-1-(4-fluorophenyl)-2-oxo-1,2-dihydropyridine-3-carboxamide (0.101 g, 0.214 mmol), 1-(2-((tert-butyldimethylsilyl)oxy)ethyl)-4-(4,4,5,5-tetramethyl-1,3,2-dioxaborolan-2-yl)-1H-pyrazole (0.098 g, 0.278 mmol) and K₂CO₃ (0.089 g, 0.642 mmol) in dioxane (2 mL) and H₂O (0.333 mL) was sparged with Ar, treated with Pd(PPh₃)₄ (0.012 g, 10.70 μmol), sparged with Ar again, and heated to 70° C. overnight. The mixture was cooled to RT, treated with satd. NaHCO₃, extracted with EtOAc (2×) and the combined organics were washed with brine, dried over MgSO₄, concentrated to dryness and purified via silica gel chromatography (EtOAc/Hex) to afford N-(4-((2-(1-(2-((tert-butyldimethylsilyl)oxy)ethyl)-1H-pyrazol-4-yl)pyridin-4-yl)oxy)-2,5-difluorophenyl)-1-(4-fluorophenyl)-2-oxo-1,2-dihydropyridine-3-carboxamide (124 mg, 88%) as a white solid. ¹H NMR (400 MHz, DMSO-d₆): δ 12.44 (s, 1H); 8.58-8.59 (m, 2H); 8.39 (d, J=5.7 Hz, 1H); 8.23 (s, 1H); 8.16 (dd, J=6.6, 2.2

Hz, 1H); 8.01 (s, 1H); 7.60-7.62 (m, 3H); 7.43 (m, 2H); 7.19 (d, J=2.5 Hz, 1H); 6.43-6.75 (m, 2H); 4.18 (t, J=5.1 Hz, 2H); 3.89 (t, J=5.2 Hz, 2H); 0.75 (s, 9H); −0.12 (s, 6H); MS (ESI) m/z: 662.3 (M+H$^+$).

A solution of N-(4-((2-(1-(2-(((tert-butyldimethylsilyl)oxy)ethyl)-1H-pyrazol-4-yl)pyridin-4-yl)oxy)-2,5-difluorophenyl)-1-(4-fluorophenyl)-2-oxo-1,2-dihydropyridine-3-carboxamide (0.121 g, 0.183 mmol) in 1.0M HCl in MeOH (2.75 mL, 2.75 mmol) was stirred at RT for 1 h. The solids were collected via filtration, rinsed with a small amount of MeOH and dried under high vacuum at 80° C. to afford N-(2,5-difluoro-4-((2-(1-(2-hydroxyethyl)-1H-pyrazol-4-yl)pyridin-4-yl)oxy)phenyl)-1-(4-fluorophenyl)-2-oxo-1,2-dihydropyridine-3-carboxamide hydrochloride (95 mg, 89%) as a white solid. $^1$H NMR (400 MHz, DMSO-d$_6$): δ 12.45 (s, 1H); 8.54-8.58 (m, 4H); 8.30 (s, 1H); 8.12 (dd, J=6.6, 2.2 Hz, 1H); 7.63-7.72 (m, 2H); 7.54-7.56 (m, 2H); 7.37 (m, 2H); 7.13 (s, 1H); 6.71 (m, 1H); 4.15 (t, J=5.3 Hz, 2H); 3.70 (t, J=5.4 Hz, 2H); MS (ESI) m/z: 548.2 (M+H$^+$).

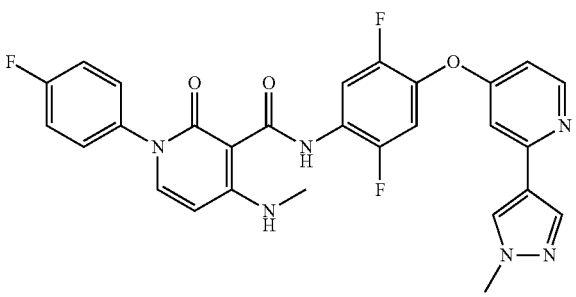 [SMILES: CNc1ccn(-c2ccc(F)cc2)c(=O)c1C(=O)Nc1cc(F)c(Oc2ccnc(-c3cnn(C)c3)c2)cc1F]

Example 4

A mixture of Example A5 (100 mg, 0.155 mmol) in a methanolic solution of MeNH$_2$ (10 mL) was heated at 80° C. for 3 h. The mixture was concentrated to dryness and purified by HPLC to afford N-(2,5-difluoro-4-((2-(1-methyl-1H-pyrazol-4-yl)pyridin-4-yl)oxy)phenyl)-1-(4-fluorophenyl)-4-(methylamino)-2-oxo-1,2-dihydropyridine-3-carboxamide (31 mg, 36%). $^1$H-NMR (400 MHz, CD$_3$OD): δ 8.64 (br, s, 1H), 8.49 (br, s, 1H), 8.42 (br, s, 1H), 8.13 (br, s, 1H), 7.64 (br, s, 3H), 7.56 (br, s, 2H), 7.37-7.16 (m, 4H), 6.33 (br, s, 1H), 3.98 (s, 3H), 3.09 (s, 3H); MS (ESI) m/z: 547.2 (M+H$^+$).

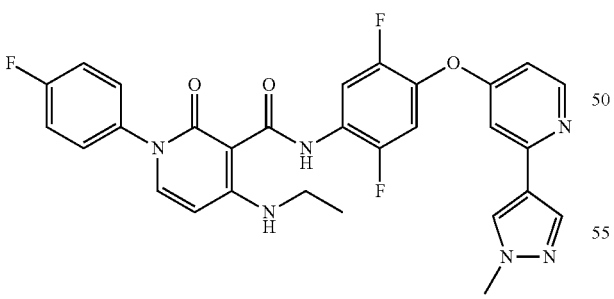

Example 5

A mixture of Example A5 (100 mg, 0.155 mmol) in a methanolic solution of ethylamine (10 mL) was heated at 80° C. for 3 h. The mixture was concentrated to dryness and purified by HPLC to afford N-(2,5-difluoro-4-((2-(1-methyl-1H-pyrazol-4-yl)pyridin-4-yl)oxy)phenyl)-4-(ethylamino)-1-(4-fluorophenyl)-2-oxo-1,2-dihydropyridine-3-carboxamide (30 mg, 34%). $^1$H-NMR (400 MHz, DMSO-d$_6$): δ 13.29 (s, 1H), 10.51 (t, J=5.2 Hz, 1H), 8.52 (m, 1H), 8.47 (d, J=6.0 Hz, 1H), 8.40 (s, 1H), 8.10 (s, 1H), 7.72 (d, J=8.0 Hz, 1H), 7.59 (dd, J=7.6, 11.2 Hz, 1H), 7.50 (d, J=5.2 Hz, 2H), 7.39 (m, 3H), 6.92 (d, J=4.4 Hz, 1H), 6.30 (d, J=8.0 Hz, 1H), 3.88 (s, 3H), 3.48 (m, 2H; obscured by water), 1.26 (t, J=7.2 Hz, 3H); MS (ESI) m/z: 561.2 (M+H$^+$).

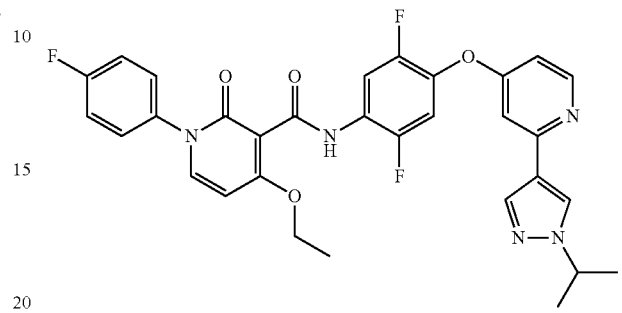

Example 6

Example A6 (200 mg, 0.388 mmol), (1-isopropyl-1H-pyrazol-4-yl)boronic acid (72 mg, 0.465 mmol) and K$_2$CO$_3$ (161 mg, 1.163 mmol) were combined in dioxane (4 mL) and H$_2$O (2 mL), sparged with Ar, treated with Pd(PPh$_3$)$_4$ (22 mg, 19 μmol) and heated at 80° C. for 5 h. The mixture was cooled to RT, treated with EtOAc and H$_2$O, filtered through diatomaceous earth and the layers of the filtrate separated. The organic layer was washed with brine, dried over Na$_2$SO$_4$, concentrated to dryness and purified via silica gel chromatography (EtOAc/Hex) to afford N-(2,5-difluoro-4-((2-(1-isopropyl-1H-pyrazol-4-yl)pyridin-4-yl)oxy)phenyl)-4-ethoxy-1-(4-fluorophenyl)-2-oxo-1,2-dihydropyridine-3-carboxamide (159 mg, 69%) as a white solid. $^1$H NMR (400 MHz, DMSO-d$_6$): δ 11.19 (s, 1H), 8.38-8.32 (m, 3H), 7.99 (s, 1H), 7.92 (d, J=7.8 Hz, 1H), 7.53-7.46 (m, 3H), 7.36 (m, 2H), 7.29 (d, J=2.5 Hz, 1H), 6.71 (dd, J=5.7, 2.4 Hz, 1H), 6.55 (d, J=7.9 Hz, 1H), 4.50 (m, 1H), 4.28 (q, J=7.0 Hz, 2H), 1.42 (d, J=6.7 Hz, 6H), 1.33 (t, J=7.0 Hz, 3H); MS (ESI) m/z: 590.2 (M+H$^+$).

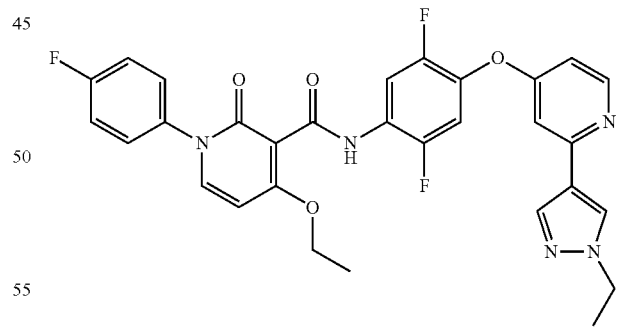

Example 7

In a sealed tube, Example A6 (200 mg, 0.388 mmol), 1-ethyl-4-(4,4,5,5-tetramethyl-1,3,2-dioxaborolan-2-yl)-1H-pyrazole (103 mg, 0.465 mmol) and K$_2$CO$_3$ (161 mg, 1.163 mmol) were combined in dioxane (4 mL) and H$_2$O (2 mL), sparged with Ar, treated with Pd(PPh$_3$)$_4$ (22 mg, 19 μmol) and heated at 80° C., for 22 h. The mixture was cooled to RT, treated with EtOAc, washed with satd. NaHCO$_3$, then brine, dried over Na$_2$SO$_4$, concentrated to dryness and purified via reverse-phase chromatography (MeCN/H$_2$O with 0.1% TFA). The organics were removed under reduced pressure and the aqueous residue neutralized with satd. NaHCO$_3$. The resulting solid was collected via filtration and dried to afford 4-ethoxy-N-(4-((2-(1-ethyl-1H-pyrazol-4-yl)pyridin-4-yl)oxy)-2,5-difluorophenyl)-1-(4-fluorophenyl)-2-oxo-1,2-dihydropyridine-3-carboxamide (96 mg, 43%) as a white solid. $^1$H NMR (400 MHz, DMSO-d$_6$): δ 11.19 (s, 1H), 8.39-8.30 (m, 3H), 7.99 (s, 1H), 7.92 (d, J=7.8 Hz, 1H), 7.54-7.45 (m, 3H), 7.37 (m, 2H), 7.26 (s, 1H), 6.72 (d, J=5.5 Hz, 1H), 6.55 (d, J=7.8 Hz, 1H), 4.28 (q, J=7.0 Hz, 2H), 4.13 (q, J=7.3 Hz, 2H), 1.35 (m, 6H); MS (ESI) m/z: 576.2 (M+H$^+$).

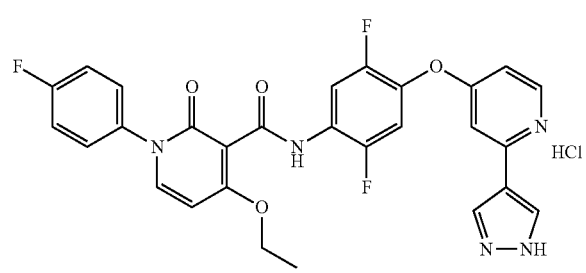 [SMILES: CCOc1ccn(-c2ccc(F)cc2)c(=O)c1C(=O)Nc1cc(F)c(Oc2ccnc(-c3cn[nH]c3)c2)cc1F ; Cl]

Example 8

In a sealed tube, Example A6 (200 mg, 0.388 mmol), 4-(4,4,5,5-tetramethyl-1,3,2-dioxaborolan-2-yl)-1H-pyrazole (113 mg, 0.582 mmol) and K$_2$CO$_3$ (161 mg, 1.163 mmol) were combined in dioxane (4 mL) and H$_2$O (2 mL), sparged with Ar, treated with Pd(PPh$_3$)$_4$ (22 mg, 19 μmol) and heated at 80° C. for 22 h. The mixture was cooled to RT, treated with EtOAc, washed with satd. NaHCO$_3$, then brine, dried over Na$_2$SO$_4$, concentrated to dryness and purified via reverse-phase chromatography (MeCN/H$_2$O with 0.1% TFA). The organics were removed under reduced pressure and the aqueous residue neutralized with satd. NaHCO$_3$. The resulting solid was collected via filtration and dried to afford N-(4-((2-(1H-pyrazol-4-yl)pyridin-4-yl)oxy)-2,5-difluorophenyl)-4-ethoxy-1-(4-fluorophenyl)-2-oxo-1,2-dihydropyridine-3-carboxamide (87 mg, 41%) as a white solid. MS (ESI) m/z: 548.1 (M+H$^+$).

To a mixture of N-(4-((2-(1H-pyrazol-4-yl)pyridin-4-yl)oxy)-2,5-difluorophenyl)-4-ethoxy-1-(4-fluorophenyl)-2-oxo-1,2-dihydropyridine-3-carboxamide (87 mg, 0.159 mmol) in MeCN (3 mL) was added 0.1 N HCl (1.59 mL, 0.159 mmol) and the solution frozen and lyophilized. The material was treated with Et$_2$O, the solid collected via filtration and dried to afford N-(4-((2-(1H-pyrazol-4-yl)pyridin-4-yl)oxy)-2,5-difluorophenyl)-4-ethoxy-1-(4-fluorophenyl)-2-oxo-1,2-dihydropyridine-3-carboxamide hydrochloride (81 mg, 79%) as a white solid. $^1$H NMR (400 MHz, DMSO-d$_6$): δ 11.28 (s, 1H), 8.54-8.37 (m, 4H), 7.93 (d, J=7.8 Hz, 1H), 7.67 (s, 1H), 7.60 (m, 1H), 7.48 (m, 2H), 7.37 (m, 2H), 7.04 (s, 1H), 6.56 (d, J=6.7 Hz, 1H), 4.28 (q, J=6.9 Hz, 2H), 1.33 (t, J=7.0 Hz, 3H); MS (ESI) m/z: 548.2 (M+H$^+$).

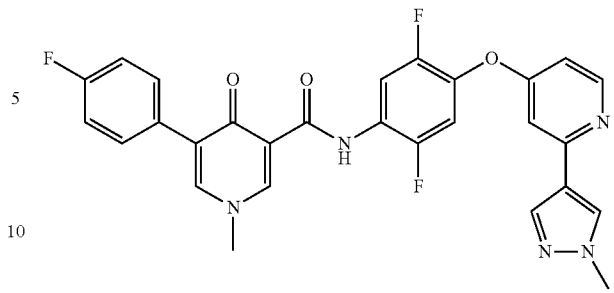

Example 9

A solution of Example A9 (0.385 g, 1.559 mmol), Example A1 (0.200 g, 0.779 mmol) and TBTU (0.751 g, 2.338 mmol) in DMF (15 mL) was treated with Et$_3$N (0.652 mL, 4.68 mmol) and stirred at RT overnight. The mixture was treated with satd. NaHCO$_3$, extracted with EtOAc (2×) and the combined organics washed with satd. NaHCO$_3$ (1×), then brine (1×), dried over MgSO$_4$, concentrated to dryness and purified via silica gel chromatography (EtOAc/Hex) to afford N-(4-((2-chloropyridin-4-yl)oxy)-2,5-difluorophenyl)-5-(4-fluorophenyl)-1-methyl-4-oxo-1,4-dihydropyridine-3-carboxamide (438 mg, 116%) as a white solid. MS (ESI) m/z: 468.1 (M+H$^+$).

N-(4-((2-chloropyridin-4-yl)oxy)-2,5-difluorophenyl)-5-(4-fluorophenyl)-1-methyl-4-oxo-1,4-dihydropyridine-3-carboxamide (0.125 g, 0.221 mmol) was combined with 1-methyl-pyrazole-4-boronic acid (0.058 g, 0.277 mmol) and K$_2$CO$_3$ (0.092 g, 0.664 mmol) in dioxane (2 mL) and H$_2$O (0.333 mL), the mixture sparged with argon, treated with Pd(PPh$_3$)$_4$ (0.013 g, 0.011 mmol), sparged again with argon, and heated to 80° C. overnight. The mixture was cooled to RT, diluted with EtOAc, washed with H$_2$O, then brine, dried over MgSO$_4$, concentrated to dryness and purified via silica gel chromatography (MeOH/DCM) to afford N-(2,5-difluoro-4-((2-(1-methyl-1H-pyrazol-4-yl)pyridin-4-yl)oxy)phenyl)-5-(4-fluorophenyl)-1-methyl-4-oxo-1,4-dihydropyridine-3-carboxamide (103 mg, 88%) as a white solid. $^1$H NMR (400 MHz, DMSO-d$_6$): δ 13.50 (s, 1H), 8.72 (d, J=2.3 Hz, 1H), 8.57 (dd, J=12.7, 7.2 Hz, 1H), 8.37 (d, J=5.7 Hz, 1H), 8.27 (s, 1H), 8.16 (d, J=2.3 Hz, 1H), 7.98 (s, 1H), 7.70 (dd, J=8.6, 5.6 Hz, 2H), 7.58 (dd, J=11.0, 7.4 Hz, 1H), 7.30-7.22 (m, 3H), 6.74 (dd, J=5.7, 2.5 Hz, 1H), 3.92 (s, 3H), 3.84 (s, 3H); MS (ESI) m/z: 532.2 (M+H$^+$).

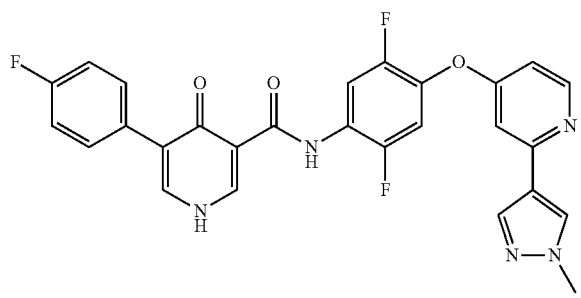 [SMILES: Cn1cc(-c2cc(Oc3cc(F)c(NC(=O)c4c[nH]cc(-c5ccc(F)cc5)c4=O)cc3F)ccn2)cn1]

Example 10

A mixture of Example A8 (0.363 g, 1.559 mmol), Example A1 (0.200 g, 0.779 mmol), and TBTU (0.751 g, 2.338 mmol) in DMF (15 mL) was treated with Et$_3$N (0.652 mL, 4.68 mmol) and stirred at RT overnight. The mixture was treated with brine, extracted with EtOAc (2×) and the combined organics were washed successively with 5% citric acid (2×), satd. NaHCO$_3$ (1×), 5% LiCl (1×), and brine (1×), dried over MgSO$_4$, concentrated to dryness and purified via silica gel chromatography (EtOAc/Hex). The resulting material was treated with 4:1 MeCN/H$_2$O, the solid collected via filtration and dried to afford N-(4-((2-chloropyridin-4-yl)oxy)-2,5-difluorophenyl)-5-(4-fluorophenyl)-4-oxo-1,4-dihydropyridine-3-carboxamide (200 mg, 54%) as a white solid. $^1$H NMR (400 MHz, DMSO-d$_6$): δ 13.48 (s, 1H), 12.72 (s, 1H), 8.60-8.58 (m, 2H), 8.30 (d, J=5.3 Hz, 1H), 8.09 (s, 1H), 7.67-7.65 (m, 3H), 7.26-7.23 (m, 2H), 7.17 (s, 1H), 7.06 (s, 1H); MS (ESI) m/z: 472.0 (M+H$^+$).

N-(4-((2-chloropyridin-4-yl)oxy)-2,5-difluorophenyl)-5-(4-fluorophenyl)-4-oxo-1,4-dihydropyridine-3-carboxamide (0.100 g, 0.212 mmol), 1-methyl-pyrazole-4-boronic acid (0.055 g, 0.265 mmol) and K$_2$CO$_3$ (0.088 g, 0.636 mmol) were combined in dioxane (2 mL) and H$_2$O (0.500 mL), sparged with argon, treated with Pd(PPh$_3$)$_4$ (0.012 g, 10.60 μmol) and heated at 80° C. for 22 h. Additional 1-methyl-pyrazole-4-boronic acid (0.055 g, 0.265 mmol) was added, the mixture sparged with argon, treated with additional Pd(PPh$_3$)$_4$ (0.012 g, 10.60 μmol) and heated at 100° C. overnight. The mixture was cooled to RT, diluted with EtOAc, filtered through diatomaceous earth and the filtrate washed with brine (2×), dried over MgSO$_4$, concentrated to dryness and purified via silica gel chromatography (MeOH/DCM) to afford N-(2,5-difluoro-4-((2-(1-methyl-1H-pyrazol-4-yl)pyridin-4-yl)oxy)phenyl)-5-(4-fluorophenyl)-4-oxo-1,4-dihydropyridine-3-carboxamide (90 mg, 82%) as a white solid. $^1$H NMR (400 MHz, DMSO-d$_6$): δ 13.48 (s, 1H), 12.72 (s, 1H), 8.63 (s, 1H), 8.57 (dd, J=12.6, 6.9 Hz, 1H), 8.37 (d, J=5.7 Hz, 1H), 8.27 (s, 1H), 8.09 (s, 1H), 7.97 (s, 1H), 7.69 (m, 2H), 7.58 (dd, J=11.1, 7.6 Hz, 1H), 7.26 (m, 3H), 6.74 (d, J=5.6 Hz, 1H), 3.84 (s, 3H); MS (ESI) m/z: 518.2 (M+H$^+$).

Biological Data c-MET Kinase Assay

Activity of c-MET kinase (Seq. ID No. 2) was determined by following the production of ADP from the kinase reaction through coupling with the pyruvate kinase/lactate dehydrogenase system (e.g., Schindler et al. *Science* 2000, 289, pp. 1938-1942). In this assay, the oxidation of NADH (thus the decrease at A340 nm) was continuously monitored spectrophotometrically. The reaction mixture (100 μl) contained c-MET (c-MET residues: 956-1390, from Invitrogen, catalogue #PV3143, 6 nM), polyE4Y (1 mg/mL), MgCl$_2$ (10 mM), pyruvate kinase (4 units), lactate dehydrogenase (0.7 units), phosphoenol pyruvate (1 mM), and NADH (0.28 mM) in 90 mM Tris buffer containing 0.25 mM DTT, 0.2% octyl-glucoside and 1% DMSO, pH 7.5. Test compounds were incubated with c-MET (Seq. ID No. 2) and other reaction reagents at 22° C. for 0.5 h before ATP (100 μM) was added to start the reaction. The absorption at 340 nm was monitored continuously for 2 hours at 30° C. on Polarstar Optima plate reader (BMG). The reaction rate was calculated using the 1.0 to 2.0 h time frame. Percent inhibition was obtained by comparison of reaction rate with that of a control (i.e., with no test compound). IC$_{50}$ values were calculated from a series of percent inhibition values determined at a range of inhibitor concentrations using software routines as implemented in the GraphPad Prism software package.

```
c-MET Kinase
                                      (Seq ID No. 2)
MSYYHHHHHHDYDIPTTENLYFQGAMLVPRGSPWIPFTMK

KRKQIKDLGSELVRYDARVHTPHLDRLVSARSVSPTTEMV

SNESVDYRATFPEDQFPNSSQNGSCRQVQYPLTDMSPILT

SGDSDISSPLLQNTVHIDLSALNPELVQAVQHVVIGPSSL

IVHFNEVIGRGHFGCVYHGTLLDNDGKKIHCAVKSLNRIT

DIGEVSQFLTEGIIMKDFSHPNVLSLLGICLRSEGSPLVV

LPYMKHGDLRNFIRNETHNPTVKDLIGFGLQVAKGMKYLA

SKKFVHRDLAARNCMLDEKFTVKVADFGLARDMYDKEYYS

VHNKTGAKLPVKWMALESLQTQKFTTKSDVWSFGVLLWEL

MTRGAPPYPDVNTFDITVYLLQGRRLLQPEYCPDPLYEVM

LKCWHPKAEMRPSFSELVSRISAIFSTFIGEHYVHVNATY

VNVKCVAPYPSLLSSEDNADDEVDTRPASFWETS.
``` c-KIT kinase Assay

Activity of c-KIT kinase (Seq. ID No. 1) was determined by following the production of ADP from the kinase reaction through coupling with the pyruvate kinase/lactate dehydrogenase system (e.g., Schindler et al. *Science* 2000, 289, pp. 1938-1942). In this assay, the oxidation of NADH (thus the decrease at A340 nm) was continuously monitored spectrophotometrically. The reaction mixture (100 μl) contained c-KIT (cKIT residues T544-V976, from ProQinase, 5.4 nM), polyE4Y (1 mg/mL), MgCl$_2$ (10 mM), pyruvate kinase (4 units), lactate dehydrogenase (0.7 units), phosphoenol pyruvate (1 mM), and NADH (0.28 mM) in 90 mM Tris buffer containing 0.2% octyl-glucoside and 1% DMSO, pH 7.5. Test compounds were incubated with c-KIT (Seq. ID No. 1) and other reaction reagents at 22° C. for less than 2 min before ATP (200 μM) was added to start the reaction. The absorption at 340 nm was monitored continuously for 0.5 hours at 30° C. on Polarstar Optima plate reader (BMG). The reaction rate was calculated using the 0 to 0.5 h time frame. Percent inhibition was obtained by comparison of reaction rate with that of a control (i.e., with no test compound). IC$_{50}$ values were calculated from a series of percent inhibition values determined at a range of inhibitor concentrations using software routines as implemented in the GraphPad Prism software package.

```
c-KIT with N-terminal GST fusion
                                      (Seq ID No. 1)
LGYWKIKGLVQPTRLLLEYLEEKYEEHLYERDEGDKWR

NKKFELGLEFPNLPYYIDGDVKLTQSMAIIRYIADKHN

MLGGCPKERAEISMLEGAVDIRYGVSRIAYSKDFETLK

VDFLSKLPEMLKMFEDRLCHKTYLNGDHVTHPDFMLYD

ALDVVLYMDPMCLDAFPKLVCFKKRIEAIPQIDKYLKS

SKYIWPLQGWQATFGGGDHPPKSDLVPRHNQTSLYKKA

GSAAAVLEENLYFQGTYKYLQKPMYEVQWKVVEEINGN

NYVYIDPTQLPYDHKWEFPRNRLSFGKTLGAGAFGKVV

EATAYGLIKSDAAMTVAVKMLKPSAHLTEREALMSELK

VLSYLGNHMNIVNLLGACTIGGPTLVITEYCCYGDLLN

FLRRKRDSFICSKQEDHAEAALYKNLLHSKESSCSDST

NEYMDMKPGVSYVVPTKADKRRSVRIGSYIERDVTPAI

MEDDELALDLEDLLSFSYQVAKGMAFLASKNCIHRDLA

ARNILLTHGRITKICDFGLARDIKNDSNYVVKGNARLP

VKWMAPESIFNCVYTFESDVWSYGIFLWELFSLGSSPY
```

```
-continued
PGMPVDSKFYKMIKEGFRMLSPEHAPAEMYDIMKTCWD

ADPLKRPTFKQIVQLIEKQISESTNHIYSNLANCSPNR

QKPVVDHSVRINSVGSTASSSQPLLVHDDV.
```

KDR Kinase Assay

Assay K1

The activity of KDR kinase was determined by following the production of ADP from the kinase reaction through coupling with the pyruvate kinase/lactate dehydrogenase system (e.g., Schindler et al. Science 2000, 289, pp. 1938-1942). In this assay, the oxidation of NADH (thus the decrease at A340 nm) was continuously monitored spectrophometrically. The reaction mixture (100 μl) contained KDR (Seq ID No. 3, 1.5 nM to 7.1 nM, nominal concentration), polyE4Y (1 mg/mL), pyruvate kinase (3.5 units), lactate dehydrogenase (5.5 units), phosphoenolpyruvate (1 mM), and NADH (0.28 mM) in 60 mM Tris buffer containing 0.13% octyl-glucoside, 13 mM $MgCl_2$, 6.8 mM DTT, test compound, and 3.5% DMSO at pH 7.5. The reaction was initiated by adding ATP (0.2 mM, final concentration). The absorption at 340 nm was continuously monitored for 3 h at 30° C. on a Polarstar Optima plate reader (BMG) or instrument of similar capacity. The reaction rate was calculated using the 1 h to 2 h time frame. Percent inhibition was obtained by comparison of reaction rate with that of a control (i.e., with no test compound). $IC_{50}$ values were calculated from a series of percent inhibition values determined at a range of inhibitor concentrations using software routines as implemented in the GraphPad Prism software package.

Assay K2

KDR kinase assay K2 is the same as for assay K1 except that (1) a nominal concentration of 2.1 nM of enzyme was employed (2) the reaction was pre-incubated with test compound at 30° C. for 2 h prior to initiation with ATP and (3) 1.0 mM ATP (final concentration) was used to initiate the reaction.

Assay K3

KDR kinase assay K3 is the same as for assay K1 except that (1) a nominal concentration of 1.1 nM of enzyme was employed, (2) the buffer components per 100 μl reaction mixture were as follows: 75 mM Tris buffer containing 0.066% octyl-glucoside, 17 mM $MgCl_2$, and 1% DMSO at pH 7.5, (3) the final concentration of DTT was 0.66 mM, (4) the reaction was pre-incubated with test compound at 30° C. for 1 h prior to initiation with ATP, and (5) 1.0 mM ATP (final concentration) was used to initiate the reaction.

```
KDR protein sequence used for screening
                                  (Seq. ID No. 3)
DPDELPLDEHCERLPYDASKWEFPRDRLKLGKPLGRGAF

GQVIEADAFGIDKTATCRTVAVKMLKEGATHSEHRALMS

ELKILIHIGHHLNVVNLLGACTKPGGPLMVIVEFCKFGN

LSTYLRSKRNEFVPYKVAPEDLYKDFLTLEHLICYSFQV

AKGMEFLASRKCIHRDLAARNILLSEKNVVKICDFGLAR

DIYKDPDYVRKGDARLPLKWMAPETIFDRVYTIQSDVWS

FGVLLWEIFSLGASPYPGVKIDEEFCRRLKEGTRMRAPD

YTTPEMYQTMLDCWHGEPSQRPTFSELVEHLGNLLQANA

QQD
```

FMS Kinase Assay

Activity of FMS kinase was determined by following the production of ADP from the FMS kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 μl) contained FMS (purchased from Millipore) (10 nM), polyE4Y (1 mg/mL), $MgCl_2$ (10 mM), pyruvate kinase (4 units), lactate dehydrogenase (0.7 units), phosphoenol pyruvate (1 mM), and NADH (0.28 mM) and ATP (500 μM) in 90 mM Tris buffer containing 0.2% octyl-glucoside and 1% DMSO, pH 7.5. Immediately, the inhibition reaction was started by mixing serial diluted test compound with the above reaction mixture. The absorption at 340 nm was monitored continuously for 4 hours at 30° C. on Synergy 2 plate reader. The reaction rate was calculated using the 3 to 4 h time frame. Percent inhibition was obtained by comparison of reaction rate with that of a control (i.e. in the absence of test compound). $IC_{50}$ values were calculated from a series of percent inhibition values determined at a range of inhibitor concentrations using software routines as implemented in the GraphPad Prism software package.

```
cFMS protein sequence (Y538-end) used for
screening
                                  (Seq. ID No. 4)
Y KYKQKPKYQV RWKIIESYEG NSYTFIDPTQ LPYNEKWEFP

RNNLQFGKTL GAGAFGKVVE ATAFGLGKED AVLKVAVKML

KSTAHADEKE ALMSELKIMS HLGQHENIVN LLGACTHGGP

VLVITEYCCY GDLLNFLRRK AEAMLGPSLS PGQDPEGGVD

YKNIHLEKKY VRRDSGFSSQ GVDTYVEMRP VSTSSNDSFS

EQDLDKEDGR PLELRDLLHF SSQVAQGMAF LASKNCIHRD

VAARNVLLTN GHVAKIGDFG LARDIMNDSN YIVKGNARLP

VKWMAPESIF DCVYTVQSDV WSYGILLWEI FSLGLNPYPG

ILVNSKFYKL VKDGYQMAQP AFAPKNIYSI MQACWALEPT

HRPTFQQICS FLQEQAQEDR RERDYTNLPS SSRSGGSGSS

SSELEEESSS EHLTCCEQGD IAQPLLQPNN YQFC
```

The activity of Compounds of Formula I in the aforementioned assays are indicated in Table 1.

TABLE 1

Activity of Compounds of Formula I in Enyzmatic Assays of cMET kinase, cKIT kinase, KDR kinase or cFMS kinase.

| Example | cMET | cKIT | KDR | FMS |
|---------|------|------|-----|-----|
| 1 | +++ | +++ | + | +++ |
| 2 | +++ | + | + | ++ |
| 3 | +++ | + | + | +++ |
| 4 | +++ | ++ | + | NT |
| 5 | +++ | + | + | ++ |
| 6 | +++ | + | + | NT |
| 7 | +++ | + | + | NT |
| 8 | +++ | + | + | NT |
| 9 | +++ | +++ | + | NT |
| 10 | +++ | +++ | ++ | NT |

NT: Not Tested;
+: $IC_{50} > 1$ uM;
++: $0.1$ uM $< IC_{50} \leq 1$ uM;
+++: $IC_{50} \leq 0.1$ uM EBC-1 Cell Culture EBC-1 cells (catalog #JCRB0820) were obtained from the Japan Health Science Research Resources Bank, Osaka, Japan. Briefly, cells were grown in DMEM supplemented with 10% characterized fetal bovine serum (Invitrogen, Carlsbad, Calif.) at 37° C., 5% $CO_2$, 95% humidity. Cells were allowed to expand until reaching 70-95% confluency at which point they were subcultured or harvested for assay use.

EBC-1 Cell Proliferation Assay

A serial dilution of test compound was dispensed into a 96-well black clear bottom plate (Corning, Corning, N.Y.). For each cell line, five thousand cells were added per well in 200 µL complete growth medium. Plates were incubated for 67 hours at 37° C., 5% $CO_2$, 95% humidity. At the end of the incubation period 40 µL of a 440 µM solution of resazurin (Sigma, St. Louis, Mo.) in PBS was added to each well and incubated for an additional 5 hours at 37° C., 5% $CO_2$, 95% humidity. Plates were read on a Synergy2 reader (Biotek, Winooski, Vt.) using an excitation of 540 nM and an emission of 600 nM. Data was analyzed using Prism software (Graph-Pad, San Diego, Calif.) to calculate $IC_{50}$ values.

EBC-1 phospho-MET ELISA

Fifteen thousand cells in DMEM supplemented with 0.5% characterized fetal bovine serum (FBS; Invitrogen, Carlsbad, Calif.) were added per well in a 96-well black clear bottom plate (Corning, Corning, N.Y.). Cells were then incubated overnight at 37 degrees Celsius, 5% $CO_2$, 95% humidity. A serial dilution of test compound was dispensed into another 96-well black clear bottom plate (Corning, Corning, N.Y.) containing DMEM supplemented with 0.5% FBS. Diluted compound was then added to plates containing cells and incubated for 6 hours at 37 degrees Celsius, 5% $CO_2$, 95% humidity. Cells were stimulated with 40 ng/mL HGF (R&D Systems, Minneapolis, Minn.) for 10 minutes, and then lysed. Phospho-MET in cell lysates was detected using the DuoSet IC Human Phospho-HGF R/c-MET ELISA (R&D Systems, Minneapolis, Minn.). Data was analyzed using Prism software (Graphpad, San Diego, Calif.) to calculate $IC_{50}$ values.

MKN-45 Cell Culture

MKN-45 cells (catalog #JCRB0254) were obtained from the Japan Health Science Research Resources Bank, Osaka, Japan. Briefly, cells were grown in RPMI 1640 media supplemented with 10% characterized fetal bovine serum (Invitrogen, Carlsbad, Calif.) at 37° C., 5% $CO_2$, 95% humidity. Cells were allowed to expand until reaching 70-95% confluency at which point they were subcultured or harvested for assay use.

MKN-45 Cell Proliferation Assay

A serial dilution of test compound was dispensed into a 96-well black clear bottom plate (Corning, Corning, N.Y.). Five thousand cells were added per well in 200 µL complete growth medium. Plates were incubated for 67 hours at 37° C., 5% $CO_2$, 95% humidity. At the end of the incubation period 40 µL of a 440 µM solution of resazurin (Sigma, St. Louis, Mo.) in PBS was added to each well and plates were incubated for an additional 5 h at 37° C., 5% $CO_2$, 95% humidity. Plates were read on a Synergy2 reader (Biotek, Winooski, Vt.) using an excitation of 540 nM and an emission of 600 nM. Data was analyzed using Prism software (GraphPad, San Diego, Calif.) to calculate $IC_{50}$ values.

MKN-45 phospho-MET ELISA

Twenty-five thousand cells in RPMI-1640 supplemented with 10% characterized fetal bovine serum (Invitrogen, Carlsbad, Calif.) were added per well in a 96-well black clear bottom plate (Corning, Corning, N.Y.). Cells were then incubated overnight at 37 degrees Celsius, 5% $CO_2$, 95% humidity. Media was then aspirated and cells were washed with PBS. A serial dilution of test compound was dispensed into another 96-well black clear bottom plate (Corning, Corning, N.Y.) containing serum-free RPMI-1640. Compound was added to plates containing cells and incubated for 6 hours at 37 degrees Celsius, 5% $CO_2$, 95% humidity. Cells were stimulated with 40 ng/mL HGF (R&D Systems, Minneapolis, Minn.) for 10 minutes, and then lysed. Phospho-MET in cell lysates was detected using the DuoSet IC Human Phospho-HGF R/c-MET ELISA (R&D Systems, Minneapolis, Minn.). Data was analyzed using Prism software (Graphpad, San Diego, Calif.) to calculate $IC_{50}$ values.

A549 Cell Culture

A549 cells (catalog # CCL-185) were obtained from the American Type Culture Collection (ATCC, Manassas, Va.). Briefly, cells were grown in DMEM supplemented with 10% characterized fetal bovine serum (Invitrogen, Carlsbad, Calif.) at 37 degrees Celsius, 5% $CO_2$, 95% humidity. Cells were allowed to expand until reaching 70-95% confluency at which point they were subcultured or harvested for assay use.

A549 Cell Migration Assay

Forty thousand cells in DMEM supplemented with 10% characterized fetal bovine serum (FBS; Invitrogen, Carlsbad, Calif.) were added per well in a 96-well black clear bottom Oris Collagen-Coated cell migration plate containing cell seeding stoppers (Platypus Technologies, Madison, Wis.). Cells were then incubated overnight at 37 degrees Celsius, 5% $CO_2$, 95% humidity. Cell seeding stoppers were removed creating an area for cell migration in the center of each well of the plate. Media was replaced with DMEM supplemented with 0.5% FBS. A serial dilution of test compound was dispensed into another 96-well black clear bottom plate (Corning, Corning, N.Y.) containing DMEM supplemented with 0.5% FBS. Diluted compound was then added to plates containing cells and incubated for 4 hours at 37 degrees Celsius, 5% $CO_2$, 95% humidity. After 4 hours, 40 ng/mL HGF (R&D Systems, Minneapolis, Minn.) was added, and the cells were allowed to migrate for 48 h. After 48 h, media was removed, and cells were washed with serum-free DMEM media. Calcein-AM (Invitrogen, Carlsbad, Calif.) was added to the cells and incubated for 20 min to fluorescently label cells. Media was removed, and serum-free DMEM was added. A plate mask (Platypus Technologies, Madison, Wis.) that obscures each well except for the area for cell migration in the center of the well was attached to the bottom of the migration plate and fluorescence was detected using a fluorescent plate reader. Data was analyzed using Prism software (Graphpad, San Diego, Calif.) to calculate $IC_{50}$ values.

Compounds of Formula I were found to exhibit inhibitory activity in one or more of the aforementioned cellular assays when evaluated at concentrations ≤10 µM. as indicated in Table 2.

TABLE 2

Activity of Compounds of Formula I in Cellular Assays.

| Example | EBC1 Proliferation | EBC1 pMET | MKN-45 Proliferation | MKN-45 pMET | A549 Migration |
|---------|--------------------|-----------|----------------------|-------------|----------------|
| 1 | +++ | +++ | +++ | +++ | ++ |
| 2 | +++ | +++ | +++ | +++ | +++ |
| 3 | NT | +++ | NT | +++ | NT |
| 4 | ++ | NT | + | NT | NT |
| 5 | ++ | NT | ++ | NT | NT |
| 6 | ++ | NT | ++ | NT | NT |
| 7 | +++ | NT | +++ | NT | NT |
| 8 | ++ | NT | ++ | NT | NT |

NT: Not Tested;
+: $IC_{50}$ > 1 uM;
++: 0.1 uM < $IC_{50}$ ≤ 1 uM;
+++: $IC_{50}$ ≤ 0.1 uM Measurements of In Vivo Activity Analysis of pMET inhibition in a MKN-45 xenograft pharmacodynamic model To examine the in vivo modulation of MET activity by compounds of formula I, MKN-45 xenograft tumors were excised at varying time points following a single oral dose. Briefly, MKN-45 cells were obtained from the Japan Health Sciences Foundation and expanded in RPMI medium which was supplemented with 20% FBS, 1% PSG (Penicillin/Streptomycin/Glutamine). The growth environment was maintained in an incubator with a 5% $CO_2$ atmosphere at 37° C. Cells were harvested and re-suspended using 50% serum-free media and 50% Matrigel® to generate a stock concentration of $5\times10^6$ cells/mL.

Seven to 8 week old female Harlan nude mice (Hsd:Athy-micNude-Fox1nu) were injected with 200 µL of cell suspension subcutaneously, just below the right axilla. All procedures carried out in this experiment were conducted in compliance with all the laws, regulations and guidelines of the National Institutes of Health (NIH). Treatment began when the mean tumor burden was approximately 300 mg. All mice were dosed with test compound by oral gavage. Plasma and tumor samples were collected from three mice at each timepoint 2, 4, 6, 8, 12, 18, and 24 hours after dosing. The level of pMET activity in the tumor was determined by standard western blot analysis. Plasma levels of MET inhibitors were determined by mass spectrometer analysis.

In this model, Example 2 afforded ≥80% inhibition of cFOS mRNA levels out to 8 h post 10 mg/kg dose.

U251 Intra-Cerebro-Ventricular Implant in Mice

To evaluate in vivo anti-cancer activity compounds of formula I in combination with fractionated, localized head radiation, an orthotopic U251-luc (Luc) human glioma carcinoma model in female outbred nu/nu mice is employed. Briefly, U251 cells are obtained from the ATCC and altered to be luciferase expressing. They are grown in RPMI 1640 Media supplemented with 10% FBS and 1% PSG. The growth environment is maintained in an incubator with a 5% $CO_2$ atmosphere at 37° C. Female Harlan Nude mice (Hsd:Athymic-Nude-Fox1nu) 8-9 weeks old are used in this study. Test animals are implanted intracranially with U251-luc (Lucm-Cherry) cells. Briefly, animals are injected subcutaneously with 5 mg/kg carprofen and anesthetized using 2% isoflurane in air. The animals are then secured in a stereotaxic frame (ASIinstruments, Inc.) and a hole drilled 2 mm right lateral, 1 mm anterior to the coronal suture. The cell suspension (stored on wet ice) is mixed thoroughly and drawn up into a 50 µl syringe. The syringe needle is centered over the burr hole and lowered 3 mm into the brain and retracted 1 mm to form a "reservoir" for the deposition of the cell suspension. 10 µl of the cell suspension ($1\times10^6$ cells/mouse) are then injected slowly into the brain tissue. Tumor progression is tracked with in vivo bioluminescence imaging performed using an IVIS 50 optical imaging system (Xenogen, Alameda, Calif.). Bioluminescence images are acquired at periodic intervals for tumor burden estimation. All procedures carried out in this experiment are conducted in compliance with all the laws, regulations and guidelines of the National Institutes of Health (NIH). Treatment begins when the mean brain bioluminescence signal for all groups in the experiment was ~$1.3\times109$ photons/sec (typically 9 days post-implant). All mice receive 2 Gy of radiation each day for five consecutive days from a RadSource RS-2000 irradiator. Additionally, mice receive test compound dosed by oral gavage or optionally with co-administered bevacizumab by tail vein injection. Bioluminescence images are acquired generally on days 8, 10, 14, 17, 21, 22, 24, 28 and 35 post-implant for tumor burden estimation. For each measurement, each mouse is injected subcutaneously with 150 mg/kg D-Luciferin (Promega) and imaged 10 minutes after the injection. Images are analyzed using Living Image (Xenogen, Alameda, Calif.) software. The BLI signal in the brain is calculated with a fixed area ROI to estimate the tumor burden. Average BLI signal for each group is compared to vehicle control to determine therapeutic benefit. Twenty-eight days after the first radiation treatment mice are euthanized, via over-exposure to carbon dioxide, for blood and brain collection. Whole blood is collected via terminal cardiac puncture and placed into EDTA Microtainer® tubes. Brains are excised and placed into 10% neutral buffered formalin.

MKN-45 Xenograft Study

To evaluate the in vivo anti-cancer activity compounds of formula I, a MKN-45 human gastric adenocarcinoma xenograft was employed. Briefly, MKN-45 cells were obtained from the Japan Health Sciences Foundation and expanded in RPMI medium which was supplemented with 20% FBS, 1% PSG. The growth environment was maintained in an incubator with a 5% $CO_2$ atmosphere at 37° C. Cells were harvested and re-suspended using 50% serum-free media and 50% Matrigel® to generate a stock concentration of $5\times10^6$ cells/mL.

Seven to 8 week old female Harlan nude mice (Hsd:Athy-micNude-Fox1nu) were injected with 200 µL of cell suspension subcutaneously, just below the right axilla. All procedures carried out in this experiment were conducted in compliance with all the laws, regulations and guidelines of the National Institutes of Health (NIH). Treatment began when the mean tumor burden was approximately 150 mg. All mice were dosed with test compound by oral gavage. Body weights and tumor measurements were recorded three times weekly. Tumor burden (mg) was estimated from caliper measurements by the formula for the volume of a prolate ellipsoid assuming unit density as: Tumor burden (mg)=(L×W2)/2, where L and W were the respective orthogonal tumor length and width measurements (mm). The primary endpoints to evaluate efficacy was % T/C. % T/C was defined as the median tumor mass of a Treated Group divided by the median tumor mass of the Control Group×100.

Example 2 was evaluated in this model and exhibited 12% T/C or 19% T/C after 14 days of twice daily dosing 30 mg/kg or 10 mg/kg, respectively.

EBC-1 Xenograft Study

To evaluate the in vivo anti-cancer activity compounds of formula I, an EBC-1 human lung carcinoma xenograft is employed. Briefly, EBC-1 cells are obtained from the Japan Health Sciences Foundation and expanded in DMEM medium which is supplemented with 10% FBS, 1% PSG. The growth environment is maintained in an incubator with a 5% $CO_2$ atmosphere at 37° C. Cells are harvested and re-suspended using 50% serum-free media and 50% Matrigel® to generate a stock concentration of $5\times10^6$ cells/mL.

Seven to 8 week old female athymic nude mice (nu/nu from Charles River) are injected with 200 µL of cell suspension subcutaneously, just below the right axilla. All procedures carried out in this experiment are conducted in compliance with all the laws, regulations and guidelines of the National Institutes of Health (NIH). Treatment begins when the mean tumor burden is approximately 150 mg. All mice are dosed with test compound by oral gavage. Body weights and tumor measurements are recorded three times weekly. Tumor burden (mg) is estimated from caliper measurements by the formula for the volume of a prolate ellipsoid assuming unit density as: Tumor burden (mg)=(L×W2)/2, where L and W are the respective orthogonal tumor length and width measurements (mm). The primary endpoint to evaluate efficacy is % T/C. % T/C is defined as the median tumor mass of a Treated Group divided by the median tumor mass of the Control Group×100.

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed is:

1. A compound of Formula I,

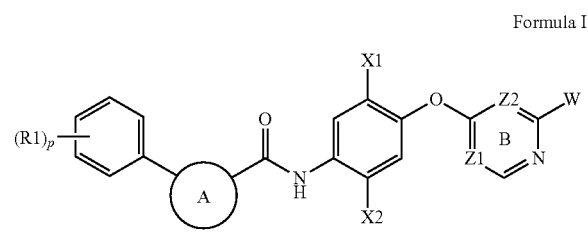

Formula I or a pharmaceutically acceptable salt, enantiomer, stereoisomer or tautomer thereof, wherein:

A is

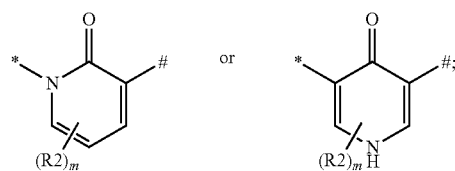

wherein the "*" is connected to the R1-substituted phenyl ring and the "#" is connected to the amide carbonyl;

W is —(CH$_2$)$_n$-pyrazole optionally substituted with —(R3)$_q$;

X1 is halogen or C1-C6 alkyl;

X2 is halogen or C1-C6 alkyl;

each R1 is individually and independently halogen, H, C1-C6 alkyl, C3-C8 branched alkyl, C3-C8 cycloalkyl, C1-C6 alkoxy, branched C3-C6 alkoxy, or cyano;

each R2 is individually and independently C1-C6 alkoxy, C1-C6 alkylamino, H, halogen, C1-C6 alkyl, C3-C8 branched alkyl, C3-C8 cycloalkyl, branched C3-C6 alkoxy, branched C3-C6 alkylamino, or cyano;

each R3 is individually and independently C1-C6 alkyl, branched C3-C8 alkyl, halogen, —(CH$_2$)$_r$—CN, —(CH$_2$)$_r$—OR6, —(CH$_2$)$_r$—NR6(R7), —(CH$_2$)$_r$—SO$_2$—C1-C6-alkyl, —(CH$_2$)$_r$—C(O)NR6(R7), —(CH$_2$)$_r$—C(O)—C4-C6-heterocyclyl, or —(CH$_2$)$_r$—C4-C6-heterocyclyl, wherein each alkyl or alkylene is optionally substituted with one or two C1-C6 alkyl;

Z1 is CR4 or N;

Z2 is CR5 or N;

with the proviso that only one of Z1 and Z2 are simultaneously N;

R4 and R5 are independently and independently H, halogen, C1-C6 alkyl, C3-C8 branched alkyl, C3-C8 cycloalkyl, C1-C6 alkoxy, branched C3-C6 alkoxy, or cyano;

each R6 and R7 is individually and independently H, C1-C6 alkyl, or branched C3-C8 alkyl;

m is 0, 1, or 2;

n is 0, 1, or 2;

p is 1, 2, or 3;

q is 0, 1, or 2; and r is 0, 1, or 2.

2. The compound of claim 1, wherein the compound is a compound of Formula Ia,

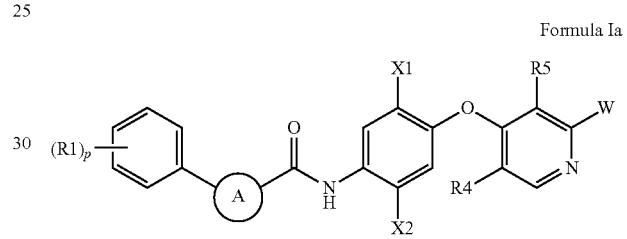

Formula Ia or a pharmaceutically acceptable salt, enantiomer, stereoisomer or tautomer thereof.

3. The compound of claim 2, wherein the compound is a compound of Formula Ib,

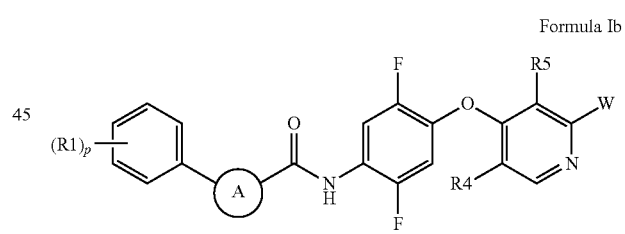

Formula Ib or a pharmaceutically acceptable salt, enantiomer, stereoisomer or tautomer thereof.

4. The compound of claim 3, wherein W is

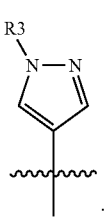

5. The compound of claim 4, wherein R3 is C1-C6 alkyl or branched C3-C8 alkyl.

6. The compound of claim 4, wherein R3 is methyl.
7. The compound of claim 3 wherein the A ring is

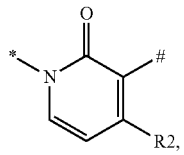

and R2 is C1-C6 alkoxy.

8. The compound of claim 7 wherein R2 is ethoxy.
9. The compound of claim 2, wherein the compound has the Formula:

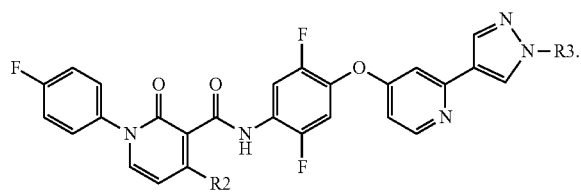

10. The compound of claim 1, wherein the compound is of Formula Ic,

Formula Ic

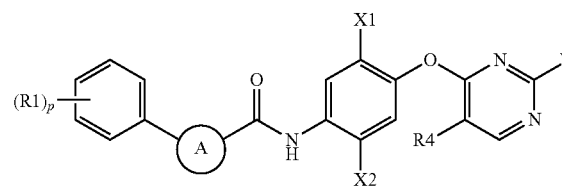

or a pharmaceutically acceptable salt, enantiomer, stereoisomer or tautomer thereof.

11. The compound of claim 10, wherein the compound is of Formula Id,

Formula Id

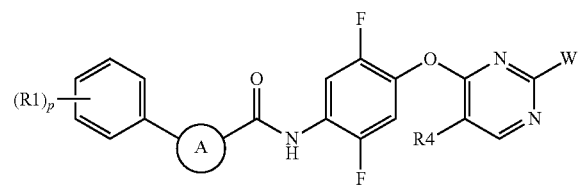

or a pharmaceutically acceptable salt, enantiomer, stereoisomer or tautomer thereof.

12. The compound of claim 11, wherein W is

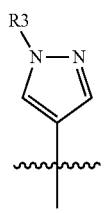

13. The compound of claim 12, wherein R3 is C1-C6 alkyl or branched C3-C8 alkyl.

14. The compound of claim 12, wherein R3 is methyl.
15. The compound of claim 11 wherein the A ring is

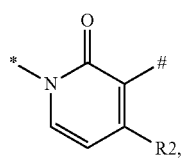

and R2 is C1-C6 alkoxy.

16. The compound of claim 15 wherein R2 is ethoxy.
17. The compound of claim 11, wherein the compound has the Formula:

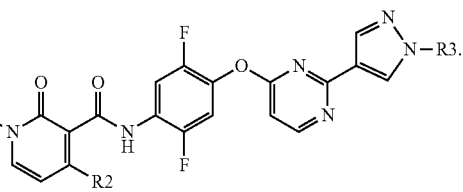

18. The compound of claim 1, wherein the compound is of Formula Ie,

Formula Ie

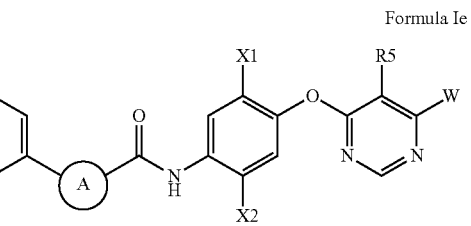

or a pharmaceutically acceptable salt, enantiomer, stereoisomer or tautomer thereof.

19. The compound of claim 18, wherein the compound is of Formula If,

Formula If

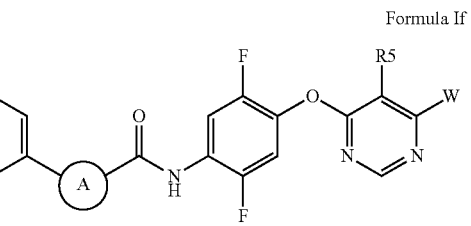

or a pharmaceutically acceptable salt, enantiomer, stereoisomer or tautomer thereof.

20. The compound of claim 19, wherein W is

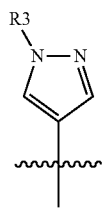

21. The compound of claim 20, wherein R3 is C1-C6 alkyl or branched C3-C8 alkyl.

22. The compound of claim 20, wherein R3 is methyl.

23. The compound of claim 19 wherein the A ring is

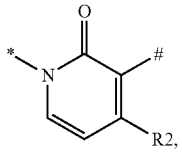

and R2 is C1-C6 alkoxy.

24. The compound of claim 23 wherein R2 is ethoxy.

25. The compound of claim 19, wherein the compound has the Formula

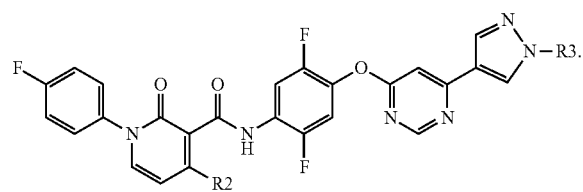

26. A compound selected from the group consisting of N-(2,5-difluoro-4-((2-(1-methyl-1H-pyrazol-4-yl)pyridin-4-yl)oxy)phenyl)-1-(4-fluorophenyl)-2-oxo-1,2-dihydropyridine-3-carboxamide, N-(2,5-difluoro-4-(2-(1-methyl-1H-pyrazol-4-yl)pyridin-4-yloxy)phenyl)-4-ethoxy-1-(4-fluorophenyl)-2-oxo-1,2-dihydropyridine-3-carboxamide, N-(2,5-difluoro-4-((2-(1-(2-hydroxyethyl)-1H-pyrazol-4-yl)pyridin-4-yl)oxy)phenyl)-1-(4-fluorophenyl)-2-oxo-1,2-dihydropyridine-3-carboxamide, N-(2,5-difluoro-4-((2-(1-methyl-1H-pyrazol-4-yl)pyridin-4-yl)oxy)phenyl)-1-(4-fluorophenyl)-4-(methylamino)-2-oxo-1,2-dihydropyridine-3-carboxamide, N-(2,5-difluoro-4-((2-(1-methyl-1H-pyrazol-4-yl)pyridin-4-yl)oxy)phenyl)-4-(ethylamino)-1-(4-fluorophenyl)-2-oxo-1,2- dihydropyridine-3-carboxamide, N-(2,5-difluoro-4-((2-(1-isopropyl-1H-pyrazol-4-yl)pyridin-4-yl)oxy)phenyl)-4-ethoxy-1-(4-fluorophenyl)-2-oxo-1,2-dihydropyridine-3-carboxamide, 4-ethoxy-N-(4-((2-(1-ethyl-1H-pyrazol-4-yl)pyridin-4-yl)oxy)-2,5-difluorophenyl)-1-(4-fluorophenyl)-2-oxo-1,2-dihydropyridine-3-carboxamide, N-(4-((2-(1H-pyrazol-4-yl)pyridin-4-yl)oxy)-2,5-difluorophenyl)-4-ethoxy-1-(4-fluorophenyl)-2-oxo-1,2-dihydropyridine-3-carboxamide, N-(2,5-difluoro-4-((2-(1-methyl-1H-pyrazol-4-yl)pyridin-4-yl)oxy)phenyl)-5-(4-fluorophenyl)-1-methyl-4-oxo-1,4-dihydropyridine-3-carboxamide, and N-(2,5-difluoro-4-((2-(1-methyl-1H-pyrazol-4-yl)pyridin-4-yl)oxy)phenyl)-5-(4-fluorophenyl)-4-oxo-1,4-dihydropyridine-3-carboxamide, or a pharmaceutically acceptable salt, enantiomer, stereoisomer or tautomer thereof.

27. The compound N-(2,5-difluoro-4-(2-(1-methyl-1H-pyrazol-4-yl)pyridin-4-yloxy)phenyl)-4-ethoxy-1-(4-fluorophenyl)-2-oxo-1,2-dihydropyridine-3-carboxamide, or a pharmaceutically acceptable salt, enantiomer, stereoisomer or tautomer thereof.

28. A pharmaceutical composition, comprising a compound of claim 27 and a pharmaceutically acceptable carrier.

29. The composition of claim 28, further comprising an additive selected from adjuvants, excipients, diluents, or stabilizers.

30. The compound 4-ethoxy-N-(4-((2-(1-ethyl-1H-pyrazol-4-yl)pyridin-4-yl)oxy)-2,5-difluorophenyl)-1-(4-fluorophenyl)-2-oxo-1,2-dihydropyridine-3-carboxamide, or a pharmaceutically acceptable salt, enantiomer, stereoisomer or tautomer thereof.

31. A pharmaceutical composition, comprising a compound of claim 30 and a pharmaceutically acceptable carrier.

32. The composition of claim 31, further comprising an additive selected from adjuvants, excipients, diluents, or stabilizers.

33. A pharmaceutical composition, comprising a compound of claim 1 and a pharmaceutically acceptable carrier.

34. The pharmaceutical composition of claim 33, further comprising an additive selected from adjuvants, excipients, diluents, or stabilizers.

* * * * *